US010614586B2

(12) United States Patent
Benedetto

(10) Patent No.: US 10,614,586 B2
(45) Date of Patent: Apr. 7, 2020

(54) QUANTIFYING USER ENGAGEMENT USING PUPIL SIZE MEASUREMENTS

(71) Applicant: Sony Interactive Entertainment LLC, San Mateo, CA (US)

(72) Inventor: Warren M. Benedetto, Foothill Ranch, CA (US)

(73) Assignee: Sony Interactive Entertainment LLC, San Mateo, CA (US)

( * ) Notice: Subject to any disclaimer, the term of this patent is extended or adjusted under 35 U.S.C. 154(b) by 0 days.

(21) Appl. No.: 15/619,367

(22) Filed: Jun. 9, 2017

(65) Prior Publication Data

US 2018/0286070 A1 Oct. 4, 2018

Related U.S. Application Data

(60) Provisional application No. 62/480,265, filed on Mar. 31, 2017.

(51) Int. Cl.
*G02B 27/00* (2006.01)
*G06K 9/42* (2006.01)
(Continued)

(52) U.S. Cl.
CPC ............... *G06T 7/62* (2017.01); *A61B 3/112* (2013.01); *G02B 27/0093* (2013.01); *G02B 27/017* (2013.01); *G06F 3/011* (2013.01); *G06F 3/013* (2013.01); *G06K 9/0061* (2013.01); *G06K 9/00604* (2013.01); *G06K 9/42* (2013.01);
(Continued)

(58) Field of Classification Search
CPC ............. G06T 7/62; G06T 2207/10152; G06T 2207/30196; G06T 2207/10004; G06F 3/013; A61B 3/112
See application file for complete search history.

(56) References Cited

U.S. PATENT DOCUMENTS

2014/0108842 A1* 4/2014 Frank ..................... G06F 17/28
713/323
2016/0299354 A1 10/2016 Shtukater
(Continued)

OTHER PUBLICATIONS

Antonio Lanata; Gaetano Valenza; Enzo Pasquale Scilingo, "Eye Gaze Patterns in Emotional Pictures", Journal of Ambient Intell. Human Comput. (2013) 4:705-715. (Year: 2013).*
(Continued)

*Primary Examiner* — Siamak Harandi
(74) *Attorney, Agent, or Firm* — Penilla IP, APC

(57) ABSTRACT

Methods and systems are provided for enabling quantification and categorization of levels of user engagement of a user while wearing a head mounted display (HMD) and being presented virtual reality (VR) content. A computer-implemented method includes presenting a VR scene to an HMD user via display of the HMD and capturing one or more images of an eye of the HMD user while the HMD user is wearing the HMD and being presented with the VR scene. The method also includes operations for analyzing the one or more images for obtaining a pupil size measurement of the eye of the HMD user and for obtaining pupil size indicators usable to correlate pupil size measurements with user engagement. The method may also determine a level of user engagement based on the pupil size measurement and the pupil size indicators.

16 Claims, 14 Drawing Sheets

(51) Int. Cl.
  *G06T 7/62*  (2017.01)
  *G06F 3/01*  (2006.01)
  *G02B 27/01*  (2006.01)
  *G06K 9/00*  (2006.01)
  *A61B 3/11*  (2006.01)

(52) U.S. Cl.
  CPC .............. *G02B 2027/0178* (2013.01); *G06T 2207/10004* (2013.01); *G06T 2207/10016* (2013.01); *G06T 2207/10152* (2013.01); *G06T 2207/30196* (2013.01)

(56) References Cited

U.S. PATENT DOCUMENTS

2016/0307038 A1  10/2016  Skogo et al.
2017/0255766 A1  9/2017  Kaehler

OTHER PUBLICATIONS

Dijkstra, Karen: "Using eye tracking to distinguish between different levels of cognitive workload", Bachelor Thesis, Dec. 31, 2011, pp. 1-17, Nijmegen, Netherlands.
Intl Search Report, PCT/US2018/023018, dated Jun. 14, 2018, 4 pages.

\* cited by examiner

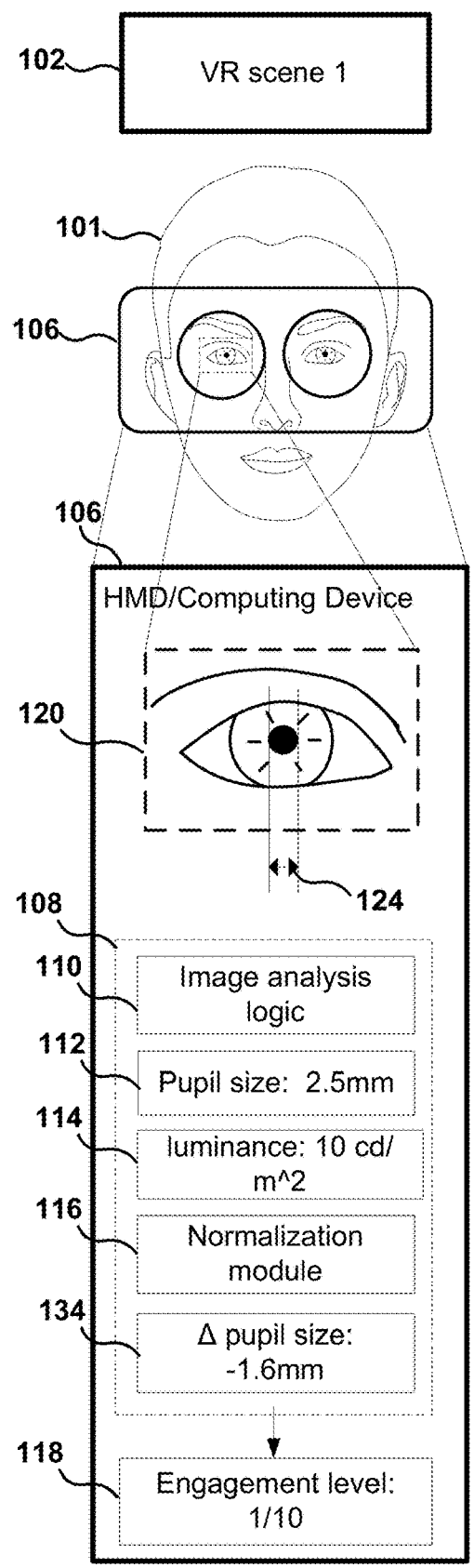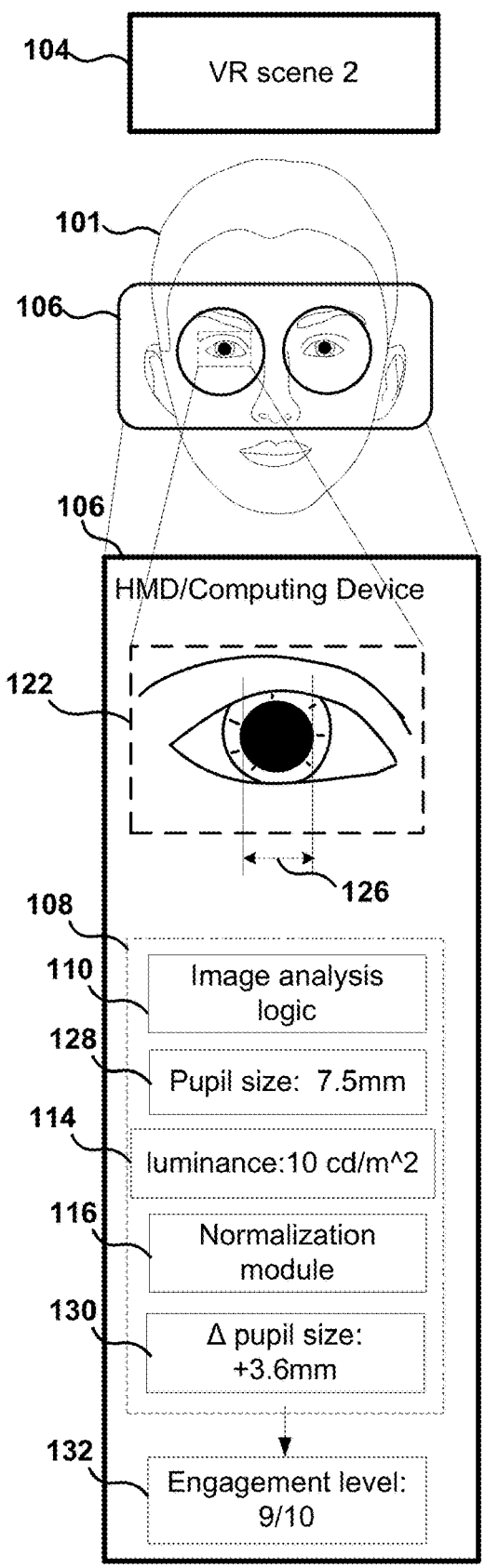
FIG. 1A
FIG. 1B

QUANTIFYING USER ENGAGEMENT USING PUPIL SIZE MEASUREMENTS

CLAIM OF PRIORITY

This application is a non-provisional of U.S. Provisional Patent Application No. 62/480,265, filed on Mar. 31, 2017, entitled "Quantifying User Engagement Using Pupil Size Measurements," which is hereby incorporated by reference.

FIELD OF THE DISCLOSURE

The present disclosure relates to virtual reality (VR) environment content presented in head mounted displays (HMDs), and methods and system for quantifying levels of user engagement in VR environments by measuring and tracking changes in pupil size of an HMD user's eyes.

BACKGROUND

Virtual reality (VR) presented through head mounted displays (HMDs) are becoming a more and more popular way for consumers to interact with various types of content. As users interact with VR content, their engagement level will tend to vary depending on the contents of a given VR scene. For example, some segments of VR content may result in higher levels of user engagement, appeal, interest, or cognitive effort, while other segments may result in lower levels of the same. Content creators and service providers stand to benefit from receiving feedback on these levels of user engagement, appeal, interest, and/or cognitive effort to better cater and appeal to their audiences. Thus, there is an opportunity to obtain feedback from HMD users in order to produce, modify, and customize VR content for HMD users in response to the feedback.

It is in this context that embodiments arise.

SUMMARY

Embodiments of the present disclosure provide for computer-implemented methods for quantifying and categorizing levels of user engagement with respect to virtual reality (VR) scenes by measuring an HMD user's pupil size. Embodiments contemplated include method operations for displaying a reference image on one or more displays associated with an HMD of the HMD user and capturing a first plurality of images of an eye of the HMD user that are indicative of a first pupil size of the HMD user. The reference image is associated with a first luminance. Generally speaking, the first pupil size may be considered an expected pupil size for a VR scene if the VR scene has a luminance that is similar to that of the reference image. Certain embodiments also include operations for displaying a VR scene to the HMD user while capturing a second plurality of images of the eye of the HMD user that are indicative of a second pupil size. The VR scene is associated with a second luminance that is similar to the first luminance. Generally speaking, the second pupil size is also considered the measured pupil size for a VR scene.

According to these and other embodiments, the first and second pluralities of images are processed for determining a difference between the second pupil size and the first pupil size. According to some embodiments, the difference between the second pupil size (the measured pupil size in response to the VR scene) and the first pupil size (the expected pupil size for the VR scene) is considered to be $\Delta$ pupil size, or a deviation between measured and expected pupil sizes.

The method is also configured to determine a level of user engagement based on the difference between the second pupil size and the first pupil size. In certain embodiments, a positive difference between the second pupil size and the first pupil size indicates a relatively high level of user engagement, whereas a negative difference indicates a relatively low level of user engagement.

In other embodiments, the reference image is part of a sequence of images within a pupillary response test segment. As a result, the first plurality of images may capture a user's pupil size in response to a range of luminance, against which a user's pupil size in response to a VR scene may be compared. For example, certain embodiments may determine a $\Delta$ pupil size that describes a difference in a measured pupil size of an HMD user while viewing a VR scene and an expected pupil size based on the luminance of the VR scene. As a result, $\Delta$ pupil size may be used to determine instantaneous levels of user engagement across a period of time in which the VR scene is displayed to the HMD user.

In another embodiment, a computer-implemented method for determining user engagement of an HMD user in response to being presented a VR scene is contemplated. According to this embodiment, the VR scene is presented to the HMD user via a display of the HMD and one or more images of the HMD user's eye is captured while the VR scene is being presented. Further, the method includes an operation for analyzing the one or more images for obtaining pupil size measurements of the eyes of the HMD user and an operation for obtaining pupil size indicators usable to correlate pupil size measurements with user engagement. The contemplated embodiment also includes an operation for determining a level of user engagement based on the pupil size measurement and the pupil size indicators.

In another embodiment, an HMD system for delivering a VR scene to an HMD user is contemplated. The HMD system includes a display configured to present the VR scene to the HMD user, as well as an image capture device configured to capture a first plurality of images of an eye of the HMD user that are unable to obtain pupil size measurements of the HMD user while the HMD user is being presented the VR scene. Moreover, in some considerations of the embodiment, the HMD system is also to include a network interface for receiving pupil size indicators to correlate pupil size measurements of the HMD user with levels of engagement of the HMD user. A memory may also be included by the HMD system to store the first plurality of images and the pupil size indicators. Further, it is contemplated that the embodiment is to include a computing device configured to analyze the first plurality of images of the eye of the HMD user to obtain pupil size measurements of the HMD user and the determine a level of user engagement based on the pupil size measurements and the pupil size indicators.

According to the embodiments discusses herein, pupil size indicators may include metrics or data that enable certain embodiments to relate pupil size readings or measurements with levels of user engagement.

Moreover, a computer program embedded in a non-transitory computer-readable storage medium, that, when executed by one or more processors for determining a level of user engagement of a HMD user to a VR scene is contemplated. The computer program, according to some embodiments, includes program instructions for presenting the VR scene to the HMD user via a display of an HMD and program instructions for capturing one or more images of an eye of the HMD user while the HMD user is wearing the HMD and being presented the VR scene, the one or more images usable to detect a pupil size of the eye of the HMD user in response to viewing the VR scene. According to certain embodiments, the computer program is to also include instructions for analyzing the one or more images for measuring the pupil size of the eye of the HMD user and for obtaining pupil size indicators usable to correlate pupil size with user engagement. Moreover, it contemplated that certain embodiments will include program instructions for determining a level of user engagement based on the pupil size and the pupil size indicators.

Other aspects of the disclosure will become apparent from the following detailed description, taken in conjunction with the accompanying drawings, illustrating by way of example the principles of the invention.

BRIEF DESCRIPTION OF THE DRAWINGS

The disclosure may best be understood by reference to the following description taken in conjunction with the accompanying drawings in which:

FIGS. 1A and 1B show a conceptual scheme of quantifying or estimating a user's level of engagement from pupil size data.

DETAILED DESCRIPTION

Figure 2A:
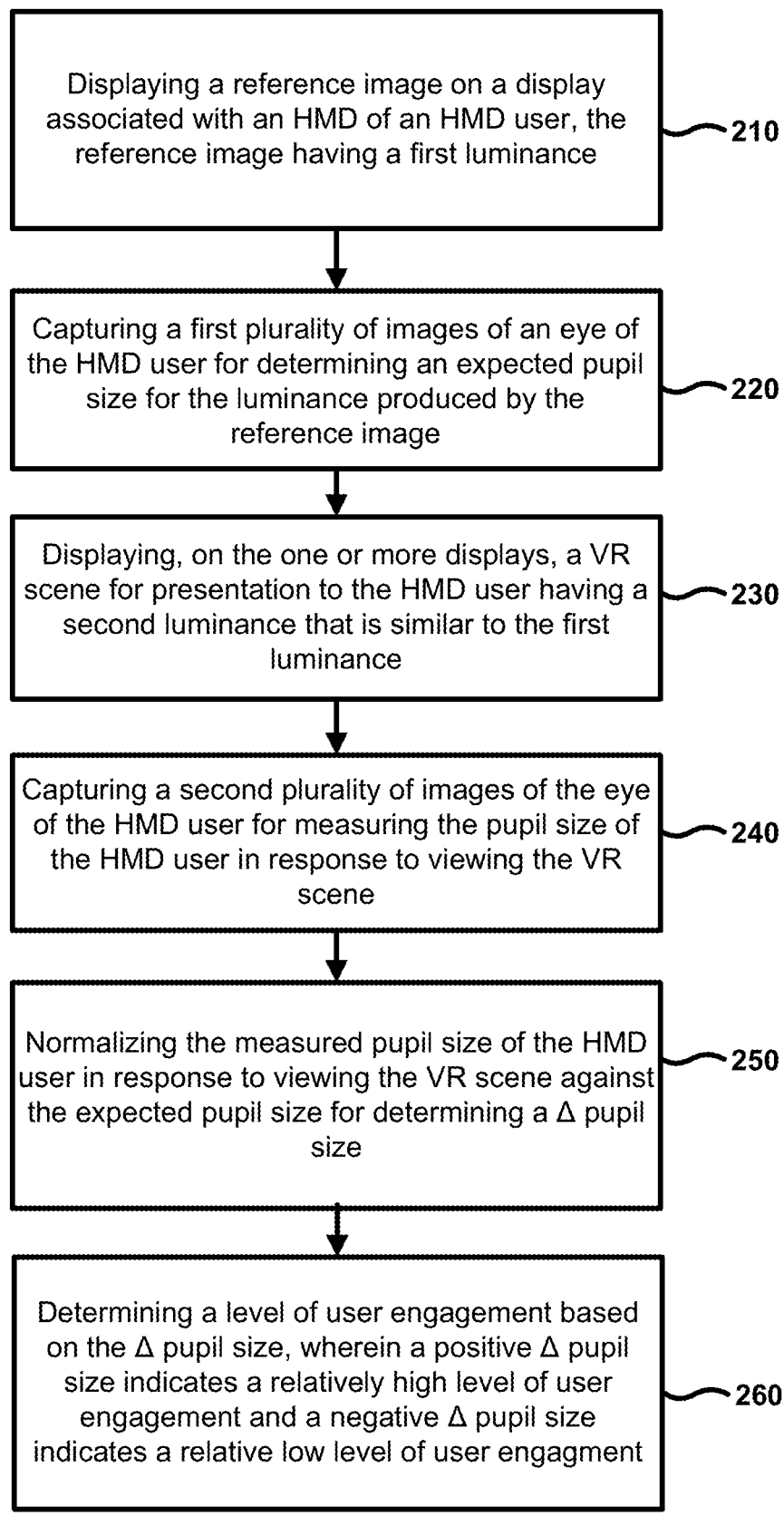
FIGS. 2A and 2B show overall flows of embodied methods for enabling determination of a level of engagement of an HMD user in response to being presented a VR scene.

The following embodiments describe methods, computer programs, and apparatus for quantifying or categorizing an HMD user's level of engagement with respect to virtual reality (VR) content by measuring pupil size of the HMD user while being presented with the VR content. It will be obvious, however, to one skilled in the art, that the present disclosure may be practiced without some or all of these specific details. In other instances, well known process operations have not been described in detail in order not to unnecessarily obscure the present disclosure.

Virtual reality (VR) environments provided by HMDs are an increasingly popular medium for consumers to interact with content and for content creators to deliver content to consumers. To provide better VR experiences to HMD users, it may be beneficial to receive feedback on an HMD user's state while interacting VR content. For example, by having feedback on the HMD user's state while interacting with VR content, content creators and consumer device manufacturers may be given a better sense of what types of content engages what types of HMD users. As a result, HMD users may be provided with more engaging content and less disengaging content. Moreover, content creators may be given a vehicle to make the VR experience a more personalized, customizable, and adaptable one for HMD users.

A user's state with respect to VR content may be defined by a number of aspects. As non-delimiting examples, some of these aspects may include the user's emotional state, level of attraction to content, level of interest in content, level of cognitive effort while interacting with content, level of frustration while interacting with content, level of satisfaction while interacting with content, a level of dizziness or sickness while interacting with content, a level of boredom while interacting with content, a level of repulsion or disinterest while interacting with content, etc. These aspects may generally be referred to herein as user engagement or levels of user engagement.

One way of estimating or quantifying user engagement is to measure the HMD user's pupil size via cameras disposed within the HMD. Generally speaking, a human's pupils will change in size by a physiological process known as pupillary response. Depending on the conditions, pupillary response includes constriction, which is a narrowing of the pupil, and dilation, which is a widening of the pupil. One of the causes of pupillary response is ambient lighting conditions in which exposure to greater levels of ambient light causes a constriction of the pupil, while exposure to low light conditions causes a dilation of the pupil.

In addition to ambient lighting conditions (e.g., luminance), human pupil size has also been shown to correlate with emotional states, levels of attraction, appeal and stimulation, cognitive intensity, etc. As a result, a user's pupil size and pupillary response may be measured and used to provide feedback on a user's state in response to VR content. For example, when normalized against VR content luminance, an increased state of pupil dilation (widening of pupil) may indicate that an HMD user has a relatively higher level of engagement (e.g., attraction, interest, appeal, cognition, etc.) to VR content being presented by the HMD. Conversely, when normalized against VR content luminance, a decrease or below expected state of pupil size (constriction or narrowing of pupil) may indicate that the HMD user has a relatively low level of engagement (e.g., boredom, repulsion, disaffection, etc.) to the VR content being presented to the HMD user.

Generally speaking, a baseline or reference for an HMD user's pupil size is used for quantifying or detecting levels of user engagement with some embodiments of the methods and systems presented here. A baseline is used in certain embodiments to differentiate or separate pupil size state changes in response to content (e.g., content-responsive or content-attributable pupillary response) from that which is in response to luminance (e.g., luminance-responsive or luminance attributable pupillary response). For example, certain embodiments may determine a difference between a measured pupil size and a baseline pupil size for estimating content-responsive pupil size changes. As a result, a normalized pupillary response (e.g., normalized against luminance) may be obtained that is attributable to content being presented to the HMD user.

As used herein, the term deviation in pupil size or Δ pupil size may be used to refer to the difference between an actual or measured pupil size in response to VR content and an expected or baseline pupil size based on luminance alone. Thus, the deviation in pupil size or the Δ pupil size is a measure of a user's reaction specifically to the VR content.

The term 'expected pupil size' is used herein to refer to a baseline pupil size that is 'expected' to occur based on luminance alone and Δ pupil size is used to refer to a deviation between measured or actual pupil size at any given moment relative to the expected pupil size. Δ pupil size may also be referred to normalized pupil size in which a measured pupil size is 'normalized' against an expected pupil size. As a result, a normalization process refers to a process in which Δ pupil size is calculated based on the difference between measured and expected pupil sizes.

Generally speaking, the expected pupil size may be determined using generally established equations that relate a range of luminance to a range of expected pupil sizes. These equations depend upon the HMD user's age, number of eyes (e.g., binocular or monocular viewing), and other parameters, and will be discussed in more detail below.

In other embodiments, the system and method presented here may use a test sequence that is presented to the HMD user via displays associated with the HMD and measure the HMD user's pupil size in response to the test sequence. For example, the test sequence may include a series of null or content-free images of varying luminance. As a result, the baseline for the HMD user's pupil size may be established while controlling for the content that is displayed during the test sequence. As referred to herein, a test sequence refers to a control segment of luminance that is generally of known magnitude.

In various embodiments, a quantification or calculation of an HMD user's level of engagement may be made based on the content-responsive or content attributable pupillary responses (e.g., Δ pupil size). Generally speaking, a greater increase or value in content-attributable pupil size is indicative of a greater level of user engagement and a greater decrease in content-attributable pupil size is indicative of a lesser degree of user engagement. Many different types of relationships between content attributable pupil dilation and constriction and user engagement may be used to establish feedback on an HMD user's state. Moreover, data obtained via other sensors for physiological activity of the HMD user may be incorporated into the quantification or categorization of the HMD user state. As a result, increased confidence levels may be obtained for HMD user state determinations, according to some embodiments.

In certain other embodiments, pupil size data obtained from an HMD user may be compared to pupil size indicators to determine levels of engagement for the user. Pupil size indicators may include data on pupil size measurements that are obtained from a community or pool of additional HMD users. It is therefore contemplated that the HMD user's level of engagement relative to a community or pool of HMD users may be estimated or established, according to some embodiments. Furthermore, in these embodiments, pupil size indicators may be used instead of or in additional to expected pupil size to establish a user's level of engagement to a particular VR scene.

FIG. 1A shows a conceptual scheme of quantifying or estimating a level of engagement of an HMD user 101 from pupil size data 112. The HMD user 101 is shown to be wearing an HMD/computing device 106 while being presented a first VR scene 102. The HMD/computing device 106 is shown to have obtained an image 120 of the HMD user's 101 left eye. Generally speaking, embodiments provided here are able to capture images for either or both eyes of the HMD user 101 (e.g., left eye only, right eye only, or both left and right eyes). Thus, although FIGS. 1A and 1B show image capture of only one eye for clarity, it is to be understood that either or both of the HMD user's 101 eyes may be measured for determining pupil size.

Also shown in FIG. 1A is a user feedback module 108, which, among other things, may provide an estimation or quantification of a level of engagement 118 of HMD user 101. Included in the user feedback module 108 are image analysis logic 110, pupil size 112, ambient luminance module 114, and normalization module 116. According to some embodiments, the image analysis logic 110 of the user feedback module 108 is able to analyze image 120 captured by an image capture device (not shown) of the HMD 106. Image analysis logic 110 is able to detect portions within image 120 that represent the HMD user's 101 pupil and portions that do not represent the pupil. As a result, image analysis logic 110 provides information as to the bounds and edges of HMD user's 101 pupils for measuring the pupil size 112.

A number of methods are contemplated for measuring pupil size 112 using image analysis logic 110, some of which have been well described in the art. For example, image analysis logic 110 may determine a distance between opposing edges or bounds of the pupil for measuring a diameter of the pupil. This contemplated embodiment is shown in FIGS. 1A and 1B. According to other embodiments, an area of the pupil may be extracted from image 120 for determining pupil size 112. There are, however, a number of other methods for measuring pupil size that may be used with the system and methods presented here without departing from the scope and spirit of the embodiments. As indicated in FIG. 1A, image analysis logic 110 is shown to determine a pupil size 112 of 2.5 mm for the HMD user 101 while being presented the first VR scene 102.

The user feedback module 108 is also shown to include a luminance module 114 and a normalization module 116, both of which function to provide content-attributable pupillary response data. For example, according to certain embodiments, luminance module 114 is able to detect or determine levels of luminance of the first VR scene 102. Generally speaking, luminance module 114 may gather data from a VR content generator (not shown), a graphics processing unit (not shown), hardware settings (not shown), gaze detection (not shown) and/or luminance sensors (not shown) of the HMD 106 to estimate an amount or intensity of light that is incident on the eyes of the HMD user 101. The amount or intensity of light that is incident on the eyes of the HMD user 101 may be referred to herein as ambient light or ambient luminance.

Typically, HMD 106 is able to present the first VR scene 102 to HMD user 101 via displays that are dedicated to each of the left eye and the right eye, which commonly are adjustable for parameters affecting luminance. Some of these parameters affecting luminance include brightness level, saturation, gamma, contrast, etc. As a result, luminance module 114 is capable of using data regarding these parameters to estimate luminance associated with the first VR scene 102, according to certain embodiments.

Moreover, the luminance of a given scene may also be affected by the content that within the images that define the first VR scene 102. For example, certain images within the first VR scene 102 may more luminous than other images. Accordingly, luminance module 114 may extract luminance data from content data of the images of the first VR scene 102 provided by a VR content generator or a graphics module that renders the images being displayed for the first VR scene 102. As a result, luminance module 114 may obtain information on the amount or intensity of light being received at the eyes of the HMD user 101 at any given moment during the first VR scene 102, according to some embodiments.

There are a number of other sources of data that luminance module 114 may also communicate with in order to estimate or measure or predict a level of luminance that is incident on a user's eyes. For example, depending upon what direction HMD user 101 is gazing at within the first VR scene 102 (e.g., where a user is looking at within the VR scene), the effective luminance for the user's eyes may change. Thus, it is contemplated in some embodiments that gaze data that tracks a user's gaze is to be used by luminance module 114 to assess luminance for either or both of the user's eyes.

Moreover, a distance between the displays associated with the HMD 106 and each of the user's eyes may also affect the amount of light that travels through the user's pupils. As a result, in certain contemplated embodiments, a proximity sensor may provide proximity data on the distance between the eyes of a user and the displays associated with the HMD 106 to the luminance module 114. As indicated in FIG. 1A, luminance module 114 determines a luminance of 10 cd/m$^2$ (candela per square meter), which reflects the amount of passing through or falling on the user's eyes.

Also shown in FIG. 1A is normalization module 116, which serves to provide a Δ pupil size 134, or normalized pupil size by normalizing the measured pupil size 112 as determined by image analysis logic 110 with luminance data determined by luminance module 114. For example, in some embodiments, normalization module 116 is enabled to determine an expected pupil size for the HMD user 101 given the luminance data provided by luminance module 114.

As noted above, determining an expected pupil size may be done in many ways, including the use of a pupillary response test segment that empirically measures pupil size as a function of luminance. Thus, according to some embodiments, normalization module 116 may receive data from the pupillary response test segment indicating that the HMD user 101 was measured for a pupil size of 3.9 mm in response to a luminance of 10 cd/m$^2$. In other embodiments, normalization module 116 may determine an expected pupil size using pupillary response models or equations. For example, the model may receive parameters including an age of the HMD user 101 and may output that the expected pupil size of the HMD user 101 is to be 3.9 mm. Both the pupillary response test segment and the pupil size model for providing an expected pupil size will be discussed in more detail below.

Normalization module 116 is configured to normalize the measured pupil size 112 against the expected pupil size given a luminance of 1 cd/m$^2$ (e.g., 3.9 mm) to provide Δ pupil size 134, which is shown to be −1.6 mm (e.g., 2.5 mm−3.9 mm=−1.6 mm) in the embodiment shown. Thus, the pupil size of the HMD user 101 is shown to be narrower or smaller than what would be expected for a luminance of 10 cd/m$^2$, which is indicative of a lack of engagement of HMD user 101 to the first VR scene 102.

User feedback module 108 is enabled to quantify, estimate, or categorize this lack of engagement to the VR scene 102 of the HMD user 101 using the data provided by each of the image analysis logic 110, the pupil size 112 of 2.5 mm, the luminance module 114, and the deviation 134 of −1.6 mm, according to the embodiment shown. A resulting engagement level 118 of 1 out of 10 is provided as an example of one of the functions of user feedback module 108.

The mechanics of determining engagement level 134 may vary depending on specific implementations of the method and system provided here, and will be discussed in more detail below. For example, there are a number of different scales or formats that engagement level 118 may conform to, as well as different models and mechanics for calculating the engagement level 118 based upon data obtained by the user feedback module 108.

FIG. 1B shows HMD user 101 being presented a second VR scene 104 that induces a relatively higher engagement level 134 of 9 out of 10. The embodiment of FIG. 1B shows the HMD/computing device 106 to have obtained an image 122 of the eye of the HMD user 101, which is subsequently analyzed by the image analysis logic 110. As previously noted, image analysis logic 110 is capable of measuring a pupil size 128 of 7.5 mm by determining a distance 126 that spans the distance between opposing edges of the pupil in image 122.

According to the embodiment shown in FIG. 1B, the luminance module 114 is shown to have determined a luminance of 10 cd/m$^2$ for the second VR scene 104. Thus, the luminance 114 for the second VR scene 104 happens to be the same as the luminance 114 for the first VR scene 102 for the sake of comparison. Also, much like the embodiment shown in FIG. 1A, the normalization module 116 is able to normalize the measured pupil size 128 of 7.5 mm against an expected pupil size for HMD user 101.

Because the first VR scene 102 and the second VR scene 104 exhibit the same luminance (e.g., 10 cd/m$^2$), the expected pupil size for HMD user 101 in FIG. 1B should be the same as that of FIG. 1B at 3.9 mm. However, because there may be a number of other factors that are incorporated by normalization module 116 to find an expected pupil size, including previous scenes displayed to HMD user 101, an amount of time that the HMD user 101 has spent viewing VR content, the expected pupil size of HMD user 101 in FIG. 1B does not necessarily have to be the same as that of FIG. 1A. Nevertheless, for the sake of clarity and comparison, it will be assumed that the expected pupil size for HMD use 101 is the same between the first VR scene 102 and the second VR scene 104.

Accordingly, the normalization module 116 is able to provide a Δ pupil size 130 of +3.6 mm (e.g., 7.5 mm-3.9 mm=+3.6 mm). As with the embodiment shown in FIG. 1A, the user feedback logic 108 is able to determine, estimate, or categorize an engagement level 132 (e.g., 9 out of 10) from the data provided by image analysis logic 110, the measurement of pupil size 128, the luminance module 114, the normalization module 116, and the deviation 130.

As compared to the engagement level 118 of HMD user 101 in response to the first VR scene 102, the engagement level 132 of the HMD user 101 to the second VR scene 104 is determined to be greater. As a result, the HMD/computing device 106 and the user feedback module 108 is able to provide feedback on an HMD user's 101 experience of VR content to determine levels of engagement relative to different VR scenes based on normalized pupil size measurements.

Although embodiments in FIGS. 1A and 1B are shown to use image data from the left eye of the HMD user 101 for clarity, it is to be understood that embodiments that are contemplated use image data from both the left and right eye of HMD user 101. For example, image analysis logic 110 may use images for both eyes to determine or measure a pupil size 112 and 128. Generally speaking, however, pupil size differences between a left and right eye of a user tend to be small.

Moreover, while embodiments in FIGS. 1A and 1B are shown to be a snapshot of a real-time process, it is to be understood that user feedback logic 108 is capable of determining levels of user engagement 118 over a period of time. Thus, HMD/computing device 106 and user feedback module 108 are configured, according to certain embodiments, to quantify, estimate, and/or categorize engagement levels in real-time to be able to relate quantified levels of user engagement to specific time points and segments of the VR scene. This is discussed in more detail below.

FIG. 2 shows an overall flow of a method for enabling determination of a level of engagement of an HMD user in response to being presented a VR scene. In operation 210, the method displays a reference image on a display associated with an HMD of an HMD user. The reference image, as noted above, may be one of a series of images within a pupillary response test segment. For example, the reference image may be a monochromatic blank image of a certain color (e.g., gray) for producing a certain luminance (e.g., 1 cd/m$^2$). Although the method of FIG. 2 is shown to display one reference image, it is to be understood that a series of reference images that make up a pupillary test segment may be used with various embodiments.

The method of FIG. 2 then flows to operation 220, which functions to capture a first plurality of images of an eye of the HMD user. According to the embodiment shown, the first plurality of images of the HMD user's eyes is indicative of the pupil size of the eyes in response to the reference image or the series of reference images. As noted above, measuring the user's pupil size in response to a reference image from a pupillary response test segment may help to establish a baseline pupil size or an expected pupil size for a given luminance. Generally speaking, the reference image or the series of reference images are to have a luminance that is similar to that of a VR scene that is to be presented to provide a more accurate expected pupil size for the VR scene.

According to the embodiment shown in FIG. 2, the method then flows to operation 230, wherein a VR scene is presented to the HMD user. Simultaneously or nearly simultaneously, operation 240 serves to capture a second plurality of images of the eye of the HMD user for measuring the pupil size of the HMD user in response to viewing the VR scene. Furthermore, operation 250 serves to normalize the measured pupil size of the HMD user in response to viewing the VR scene against the expected pupil size to obtain a Δ pupil size.

Generally speaking, Δ pupil size, or normalized pupil size, describes a deviation (if any) or difference between the measured pupil size and an expected pupil size. For example, in some embodiments, Δ pupil size may be calculated as Δ pupil size=measured pupil size—expected pupil size. As a result, Δ pupil size describes and quantifies a physiological phenomenon of increased or decreased pupil size that is caused by VR content (e.g., content-attributable or content-responsive pupillary response).

The method then flows to operation 260, which serves to determine a level of user engagement using Δ pupil size obtained in operation 250. Generally speaking, a higher/positive Δ pupil size is indicative of a relatively high level of user engagement, whereas a lower/negative Δ pupil size is indicative of a relatively low level of user engagement. As noted above, a positive Δ pupil size indicates that a user's pupils are dilated more than what would be expected based on luminance alone. As a result, a positive Δ pupil size provides an indication that the VR content has caused the user to be relatively engaged (e.g., more attracted, more interested, more cognitive exertion, etc.).

In contrast, a negative Δ pupil size indicates that a user's pupils are more constricted that what would be expected based on luminance alone. As a result, a negative Δ pupil size provides an indication that the VR content has caused the user to be relatively disengaged or disaffected (e.g., repulsed, bored, or sick). Thus, operation 260 is configured to provide a quantification or categorization of a user's level of engagement based on Δ pupil size.

Figure 2B:
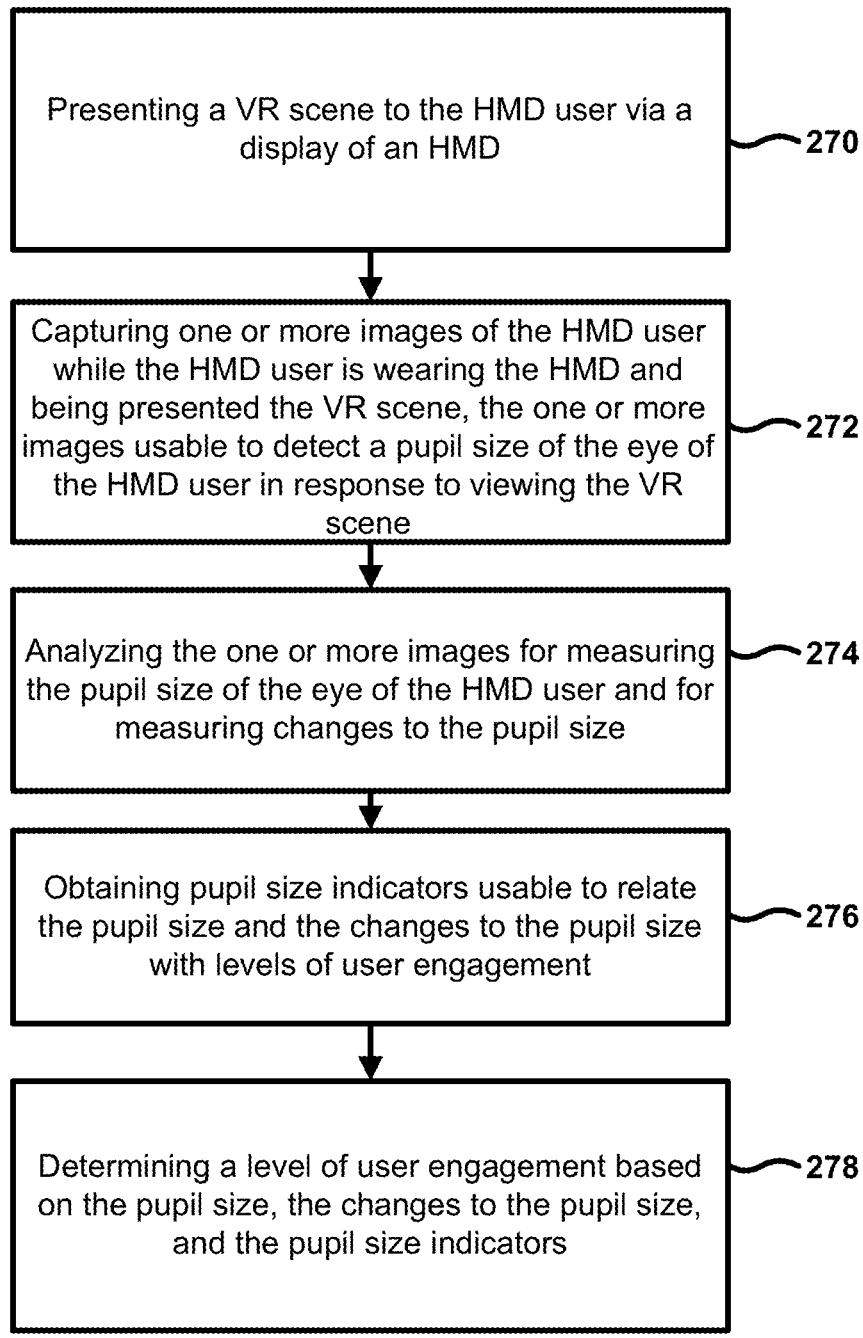

FIG. 2B shows an overall flow of an embodied method for determining an HMD user's level of engagement with respect to a VR scene using pupil size indicators. For example, the method includes an operation 270 to display a VR scene to the HMD user via a display of an HMD and an operation 272 to capture one or more images of the HMD user while the HMD user is wearing the HMD and being presented the VR scene, the one or more images usable to detect a pupil size of the eye of the HMD user in response to viewing the VR scene or content.

The method then flows to operation 274, which is shown to analyze the one or more images for measuring the pupil size of the eye of the HMD user and for measuring changes to pupil size. According to the embodiment shown in FIG. 2B, the method then flows to operation 276, in which the method obtains pupil size indicators that may be used to relate measured pupil sizes and/or changes to pupil sizes with levels of user engagement. Further, it is contemplated that the method is to also include an operation 278 for determining a level of user engagement based on the pupil size, the changes to the pupil size, and the pupil size indicators.

According to these and other embodiments, pupil size indicators are understood to be relationships, functions, graphs, models, algorithms, and/or metrics that enable an estimation of a user's level of engagement based upon pupil size measurements and/or changes to pupil size measurements.

Figure 3:
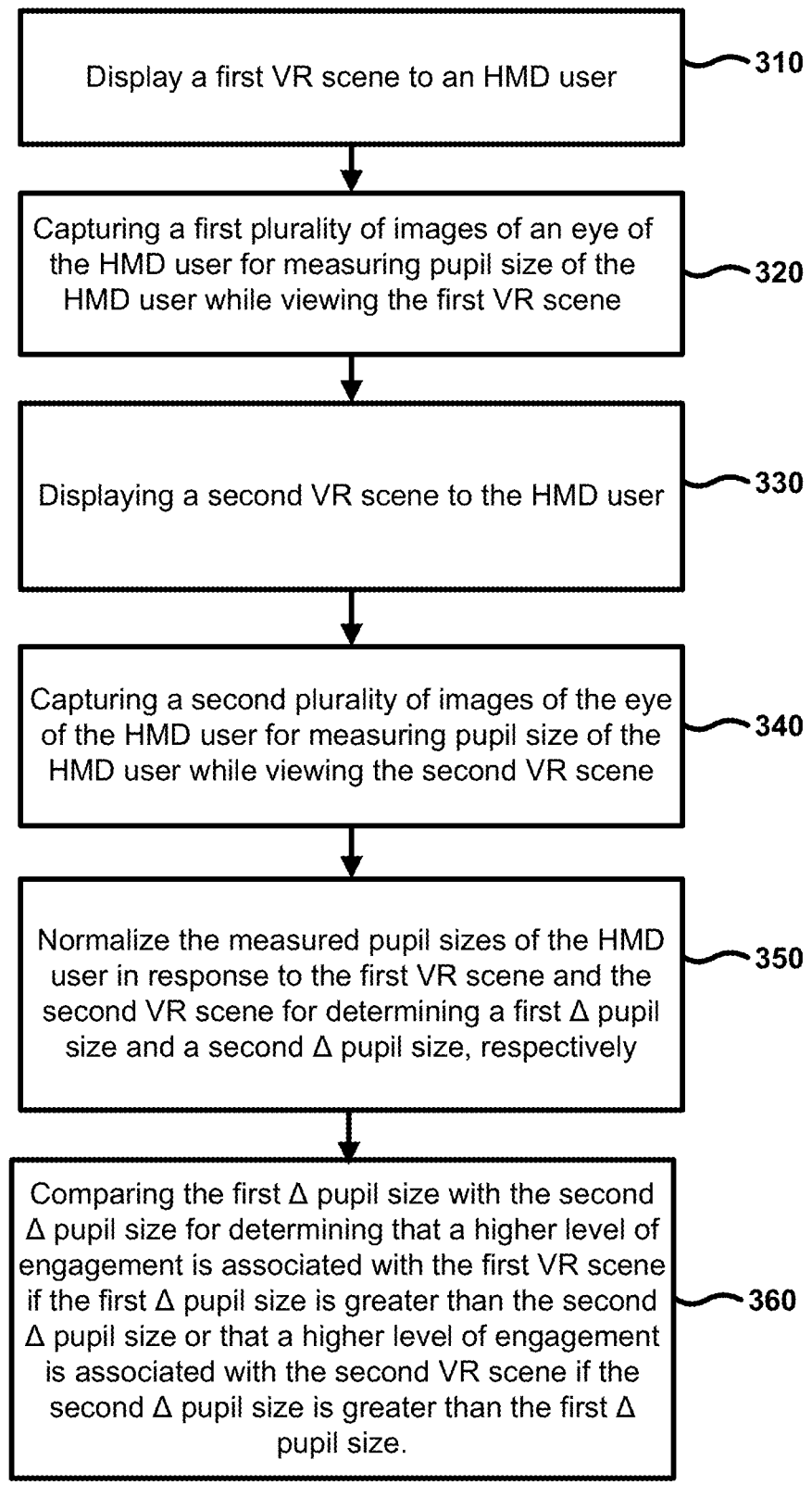
FIG. 3 shows an overall flow of a method for comparing engagement levels for two different VR scenes.

FIG. 3 shows an overall flow of a method for comparing engagement levels for two different VR scenes. In operation 310, the method displays a first VR scene an HMD user and simultaneously or nearly simultaneously captures a first plurality of images of an eye of the HMD user for measuring pupil size of the HMD user while viewing the first VR scene in operation 320. The method then flows to operation 330, in which a second VR scene is displayed or presented to the HMD user while operation 340 simultaneously or nearly simultaneously captures a second plurality of images of the eye of the HMD user for measuring pupil size of the HMD user while viewing the second VR scene.

The method provided by FIG. 3 is then shown to flow to operation 350, in which the measured pupil sizes of the HMD user in response to the first and second VR scenes are normalized against an expected pupil size for the first and second VR scenes, respectively. Operation 350 is therefore able to provide a first Δ pupil size and a second Δ pupil size. The first Δ pupil size and the second Δ pupil size is then utilized by operation 360 for a comparison that helps to determine whether the first VR scene is associated with a higher level of user engagement than the second VR scene is, or whether the second VR scene is associated with a higher level of user engagement than the first VR scene is. As noted above, Δ pupil size for a particular VR scene is proportional to the level of user engagement for the VR scene. As a result, operation 360 is able to determine which VR scene is associated with higher or lower level of user engagement by comparing the values of the first and second Δ pupil sizes.

For operation 360 of the method featured in FIG. 3, if the first Δ pupil size is determined to be greater in value than the second Δ pupil size, then operation 360 may provide that the first VR segment is associated with a higher level of user engagement than the second VR segment. If, on the other hand, it is determined that the second Δ pupil size is greater in value than the first Δ pupil size, then operation 360 may provide that the second VR segment is associated with a higher level of user engagement than the first VR segment. That is, the method is able to determine which of the two VR segments is more appealing, more interesting, requires more cognitive effort, etc. to the HMD user. As a result, the method may be useful in a number of applications to determine what content is more engaging and what content is less engaging.

For example, if it is desired to know which of two potential advertisements should be 'aired' to an audience of HMD users, it would be possible to know which of the two is more engaging to given HMD users using the method presented in FIG. 3 without needing explicit feedback from the HMD users. For example, it is possible to obtain information on which of the two advertisements is more appealing to a population of users on a physiological level without requiring feedback from the population using the method and system described here.

As a result, the method shown in FIG. 3, may allow content creators and advertisers to present content or advertisements with more appeal than they would be without the method or system described here. Moreover, embodiments may also allow HMD users to provide feedback to content creators and advertisers as to what they find interesting without needing to provide explicit feedback. In some applications using the methods and systems provided herein, a 'pay-per-appeal' or a 'pay-per-engagement' model may be used by content providers or ad publishers for implementing advertisements. More on the pay-per-appeal model of advertising will be discussed in the following.

As a In other embodiments, the method may be used to gather feedback for VR games to determine which types of scenes, heroes, avatars, weapons, tasks, rewards, graphics, characters, gameplay mechanics, and so one are more likely to engage users. It is also contemplated that VR environments such as VR games may be more personalized, customized, and adaptive to create VR experiences that are more likely to increase engagement levels. In each of these example applications of the method of FIG. 3, the method may be performed across a population of HMD users to gather enough feedback that is representative of the HMD user community as a whole, or segments of the HMD user community.

Figure 4:
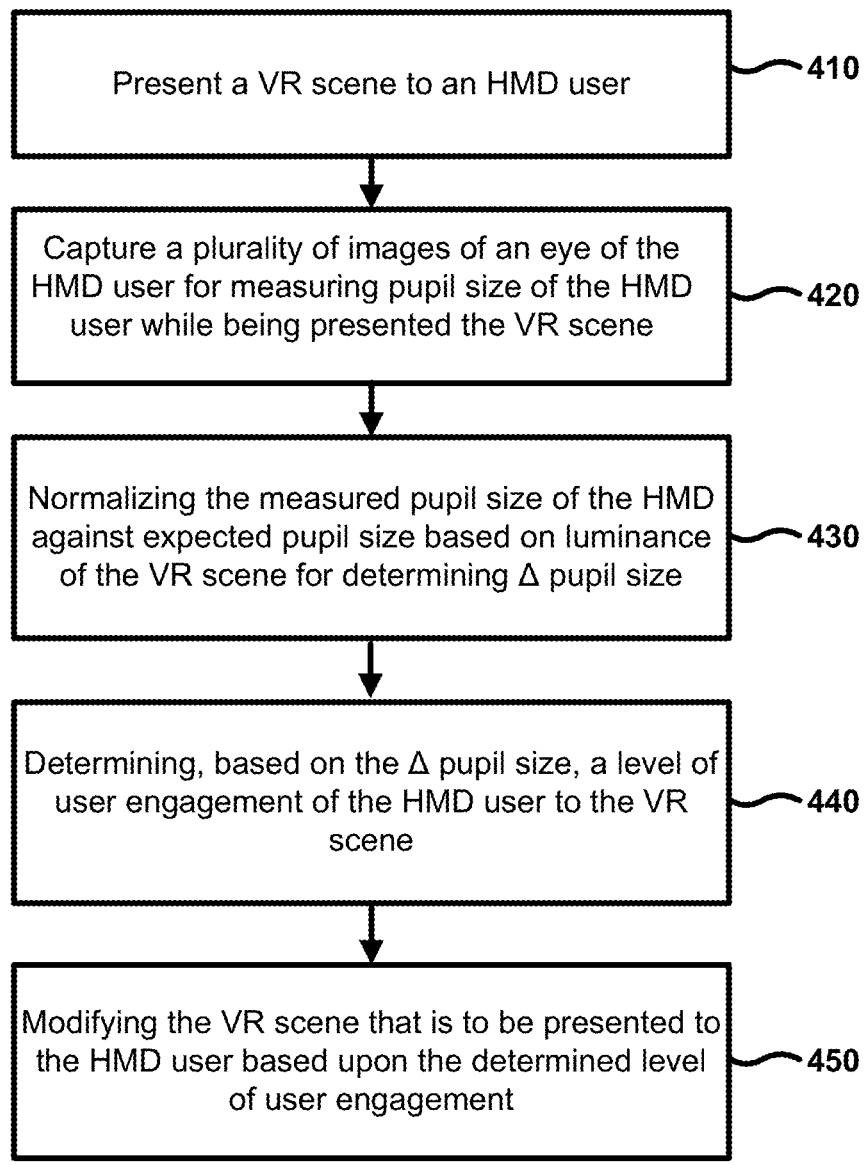
FIG. 4 shows an overall flow of a method for enabling a modulation of a VR scene for an HMD user in response to determining a level of engagement of the HMD user.

FIG. 4 shows an overall flow of a method for enabling a modulation of a VR scene for an HMD user in response to determining a level of engagement of the HMD user. The method shown in FIG. 4 includes operations 410, 420, 430, and 440, which function to display a VR scene and determine a level of user engagement, similar to the methods shown in FIGS. 2 and 3. FIG. 4, however, includes an additional operation in step 450 for modifying the VR scene that is to be presented to the HMD user based upon the determined level of user engagement. As a result, the VR scene may be modulated or throttled for intensity, content, complexity, difficulty, and the like, based upon feedback obtained from the HMD user.

For example, according to some embodiments, if an HMD user is experiencing too much difficulty progressing within a VR game, it may be beneficial to reduce a complexity or difficulty level of the VR game. In this scenario, a level of cognitive effort given by the HMD user may be relatively high, which may be considered one of the forms of user engagement. As a result, the high level of cognitive effort or engagement may be detectable using, for example, the method shown in FIG. 4 (e.g., by determining Δ pupil size). The method of FIG. 4 is capable of then modulating or throttling the difficulty or complexity level of the VR game, for example, by providing one or more hints, reducing a difficulty of a task to be completed, making a VR world more easily navigable, decreasing a number of enemies, increasing a number of allies, making an asset easier to find or obtain, making a power easier to obtain, and so on.

There are a number of additional embodiments of applications for the method of FIG. 4 that may up-regulate (e.g., increase) an intensity or difficulty of a future state of the VR scene in response to detecting a relatively low level of engagement and down-regulate (e.g., decrease) the intensity or difficulty in response to detecting a relatively high level of engagement of the HMD user to the VR scene. For example, it is contemplated that detecting a low level of user engagement (e.g., boredom) may cause a future VR scene to be modified in aspects of intensity, graphics, difficulty, and/or content. As a result, a more engaging VR experience may be obtained by using the method provided by FIG. 4 for modifying the VR scene in response to obtaining pupil size feedback.

According to some embodiments, a VR scene may be modified by changing aspects of the VR scene related to lighting, texture, resolution, a quantity a content items, realism, dynamism, motions of objects, difficulty of a task, a number of enemies, an ease of navigating, a pace of the VR scene, a difficulty progressing, among others. As a result, there a number of ways of modifying VR scenes according to pupil size measurement feedback that may enhance the VR experience by making it a more comfortable and personalized one.

Figure 5:
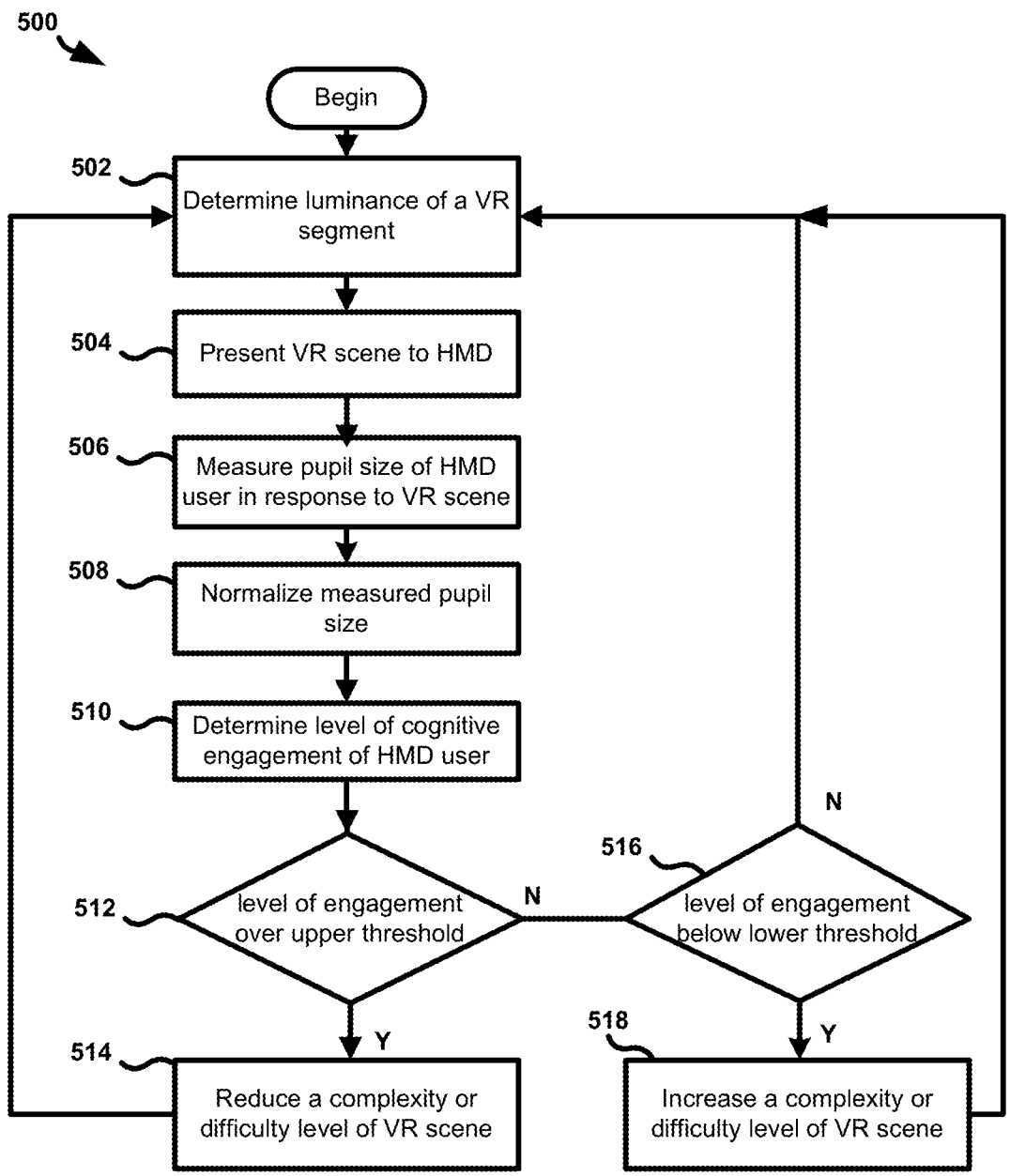
FIG. 5 shows a flow chart of a method for increasing or reducing a complexity or difficulty level of a VR scene in response to a detected level of cognitive engagement of an HMD user being presented the VR scene.

FIG. 5 shows a flow chart of a method for increasing or reducing a complexity or difficulty level of a VR scene in response to a detected level of cognitive engagement of an HMD user being presented the VR scene. According to the embodiment shown, after the method 500 determines a level of cognitive engagement at 510 by flowing through steps 502-508, the method determines if the level of determined engagement is over a threshold at 512. The upper threshold used at step 512 will depend upon a number of factors, including the content being presented at 504, the user's profile and/or history, the user settings, data gathered from other users, etc. For example, if a first user has a history of being discouraged by VR scenes that require a higher level of cognitive engagement (e.g., the first user avoids harder challenges or quits a VR game if it is too difficult), the upper threshold used at step 512 may be lower than that of a second user who has a history of not being discouraged by VR scenes requiring higher levels of cognitive engagement (e.g., the second exhibits more persistence when presented with challenging tasks within VR games).

If it determined that the user's level of cognitive engagement is above the upper threshold (e.g., "yes" at step 512), the method 500 then flows to step 514, which serves to reduce a complexity or difficulty level of the VR scene. As noted above, reducing a complexity level or difficulty may include modifying or adjusting parameters associated with the VR game that make in game tasks easier to complete, assets easier to obtain, enemies easier to defeat, puzzles easier to solve, VR landscapes easier to navigate, and so on. Once operation 514 reduces the complexity of difficulty level of the VR scene, the method then flows back to step 502.

On the other hand, if it is determined that the user's level of engagement is below a threshold (e.g., "no" at step 512), then the method flows to step 516, which determines if the user's level of engagement is below a threshold. A noted earlier, the lower threshold used may be also based a number of factors, including type of content, the user's preferences and/or settings, the user's history, and data gathered on the VR scene from other users. If it is determined that the level of cognitive engagement is below a lower threshold, the method then flows operation 518, which is configured to increase a complexity or difficulty level of the VR scene. Once the VR scene is adjusted to increase the complexity or difficulty level of the VR scene, the method 500 then flows back to step 502. However, if it is determined that the level of cognitive engagement is above a lower threshold (and below an upper threshold), then the method 500 flows back to step 502.

Figure 6:
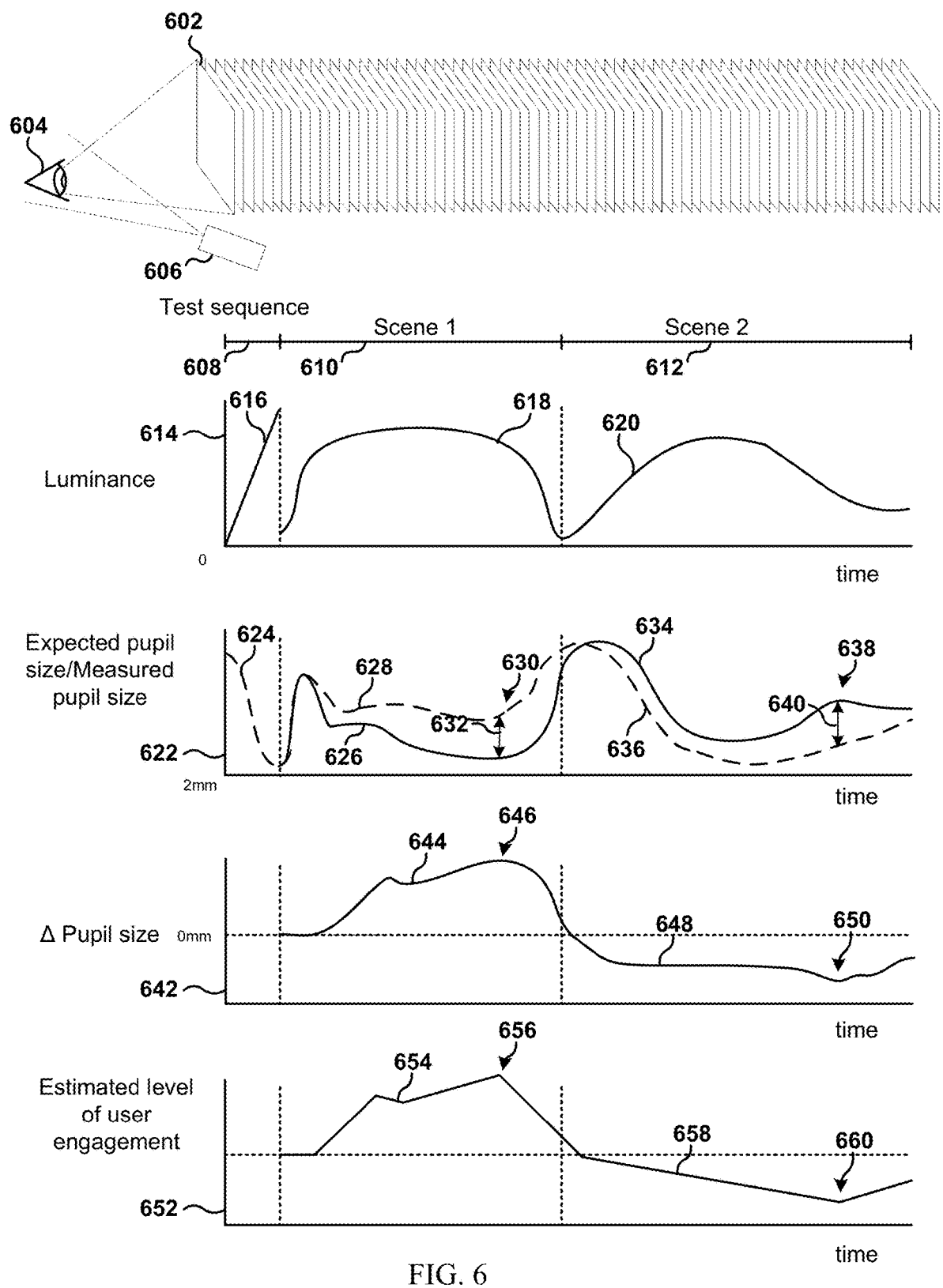
FIG. 6 shows a scheme of quantifying user engagement while an HMD user is viewing VR content.

FIG. 6 shows a scheme of quantifying levels of user engagement 652 over a period of time while an HMD user is viewing VR content 602. VR content 602 is shown to be presented to an eye 604 of an HMD user while an image capture device 606 captures images of the eye 604 and more particularly the pupil of eye 604. Although only one eye and one series of images are shown in FIG. 6, it is to be understood that a similar process may implemented for the second eye of the HMD user.

VR content 602 is shown to include a test sequence 608, which may be a pupillary response test segment, a first scene 610, and a second scene 612. Luminance 614 plots the luminance provided by VR content 602 over a period of time and represents the amount or intensity of light that is being received by the user's eye 604. For example, test sequence luminance is shown to start at or near 0 and increase to a high-end.

Generally speaking, the test sequence should include a luminance range that spans at least the luminance range of the VR content 602. For example, if the luminance range for the VR content is between 10E-3-10E3 cd/m$^2$ (e.g., the 'darkest' image within the VR content 602 provides a luminance of no less than 10E-3 cd/m$^2$, and the 'brightest' image no greater than 10E3 cd/m$^2$), then the test sequence 608 may have a luminance range that spans at least from 10E-3 to 10E3 cd/m$^2$, according to some embodiments. In this manner, an expected pupil size may be determined empirically for the range of luminance values that images within the VR content 602 may comprise of. However, as discussed above, there are other ways to estimate expected pupil size for a given luminance that may be used with the scheme shown in FIG. 6.

According to some embodiments, the plot of luminance 614 with respect to time is contemplated to be on a logarithmic scale in the embodiment shown. Generally speaking, luminance of VR content may range several orders of magnitude. As a result, some embodiments may have the test sequence to increase (or decrease) in luminance at an exponential rate. Further, although the luminance of the test sequence is shown to increase monotonically, other embodiments of tests sequences may be associated with luminance that decreases monotonically, or that are not monotonic (e.g., that increase and then decrease, or that decrease and then increase).

Moreover, while the embodiment shown in FIG. 6 includes a test sequence that reflects an exponentially defined dynamic luminance, there are any number of test sequences that may be used with the methods and systems described here without departing from the scope or spirit of the embodiments, as long as they are able to test a user's pupillary response for a range of luminance for establishing expected pupil sizes. For example, some test sequences may be associated with a range of luminance described by a linearly increasing or decreasing function, a sinusoidal function, a sigmoidal function, a Gaussian function, a polynomial function, a step function, a Cantor function, etc. It will be appreciated by one skilled in the art that any number of test sequences may be used with the embodiments described here.

After some period of time, the test sequence 608 will terminate while the first scene 610 will begin. The period of time associated with the test sequence 608 will depend on a number of factors, but may be between about 0.5 seconds long to about 10 seconds long, for some embodiments. Optionally, the first scene 610 may begin to load or buffer during the period of time associated with test sequence 608.

First scene luminance 618 is shown to increase from a lower luminance to a higher luminance initially. First scene luminance 618 is then shown to decrease back to a lower luminance at which point the first scene 610 terminates and the second scene 612 begins. Much like the first scene luminance 618, second scene luminance 620 is shown to increase to a higher luminance before declining to a lower luminance, according to the embodiment shown.

Expected and measured pupil size 622 shows a plot of a first scene expected pupil size 626, a second scene expected pupil size 634, a test sequence measured pupil size 624, a first scene measured pupil size 628, and a second scene measured pupil size 636. The test sequence measured pupil size 624 is a measurement of pupil size in response to the test sequence 608. Since test sequence 608 has a test sequence luminance 616 that begins with a lower luminance and ends with a higher luminance, the test sequence measured pupil size 624 accordingly begins at a larger pupil size that decreases to a smaller pupil size over the period of the test sequence 608.

The test sequence measured pupil size 624 may provide empirical data for establishing expected pupil sizes for a range of luminance associated with the first scene 610 and the second 612 and others. For example, if the first scene 610 includes images that are associated with a luminance of about 10E2 cd/m$^2$, the test sequence measured pupil size 624 may contain a data point that correlates the luminance of about 10E2 cd/m$^2$ with a measured or extrapolated pupil size of about 2.5 mm. As a result, an expected pupil size based on luminance-attributable pupil size may be established. A similar process may be used to establish expected pupil sizes for a range of luminance associated with the first scene 610 and the second scene 612 by using test sequence measured pupil size 624.

Thus, from the test sequence measured pupil size 624, the first scene expected pupil size 626 and second scene pupil size 634 may be established. First scene expected pupil size 626 is shown to reflect an initial pupil size that is small (e.g., constricted) due to a residual response to the high luminance at which test sequence 608 terminates. The first scene pupil size 626 is then shown increase (e.g., dilate) due to a sudden decrease in luminance as first scene begins. However, as first scene 610 progresses, first scene luminance 618 is also shown to increase sharply and generally remain at a higher luminance. As a result, the first scene expected pupil size 626 is shown to decrease sharply and remain in a lower pupil size state for the majority of the span of the first scene 610. Toward the end of the first scene 610, first scene luminance is shown to fall (e.g., appear to be less 'bright') as the first scene 610 terminates and as second scene 612 beings. As a result of the decrease in luminance, the first scene expected pupil size 626 is shown to increase as a response.

Also shown in the expected pupil size and measured pupil size 622 plot is a first scene measured pupil size 628, which is shown to track the first scene expected pupil scene 628 for a period at the beginning of the first scene 610. However, after this period, the first scene measured pupil size 628 exhibits a measurably different behavior than the first scene expected pupil size 626. In particular, first scene measured pupil size 628 is shown to be consistently higher than the first scene expected pupil size 626. That is, the user's eye is more dilated while viewing the first scene 610 than would be expected from the luminance of the first scene 610 alone, which may be indicative that the user has a relatively engaged to the first scene 610 due to the content of the first scene 610.

As noted above, the difference between the measured pupil size and the expected pupil size may be quantified as Δ pupil size, a plot for which is shown in Δ pupil size plot 642. For example, Δ pupil size plot 642 is shown to include a first scene Δ pupil size 644, which begins at about 0 mm for the period in which the first scene measured pupil size 628 is no different than the first scene expected pupil size 626. However, after this period, first scene Δ pupil size 644 is shown to increase in value and stay positive for the remainder of the first scene 610. The consistent positive value for the first scene Δ pupil size 644 may indicate that the user has a relatively high level of engagement with the first scene 610 (e.g., the user is shows interests, appeal, attraction, and/or cognitive engagement with the first scene 610).

Moreover, there is an apex 646 of first scene Δ pupil size 644 corresponding to a point 630 within the first scene 610 having a maximum difference 632 between the first scene measured pupil size 628 and the first scene expected pupil size 626. According to some embodiments, the apex 646 and point 630 may represented a point within the first scene 610 that represents a local maxima of user engagement (e.g., a scene or point within a scene at which the user is most engaged). Thus, it is possible using the method and system presented here to not only track levels of user engagement in real-time, but also to identify segments or portions of scenes that cause the greatest levels of user engagement. Such feedback data may allow content creators to know which particular scenes and events within, for example, a VR game, cause the most appeal, interest, and/or cognitive engagement for HMD users.

Estimated level of user engagement 652 is shown to include a plot of the first scene level of engagement 654 and the second scene level of engagement 658. Generally speaking, the levels of user engagement are proportional to Δ pupil size 642. For example, according to some embodiments, a small positive Δ pupil size corresponds to a small positive level of user engagement (e.g., user is mildly engaged), while a large positive Δ pupil size corresponds to a large positive level of user engagement (e.g., user is highly engaged).

Conversely, according to some embodiments, a small negative Δ pupil size may correlate with a small negative level of user engagement (e.g., user is mildly disengaged), while a large negative Δ pupil size corresponds to a large negative level of user engagement (e.g., user is highly disengaged). As a result, the first scene level of engagement 654 is seen to begin at a baseline before reaching an apex 656 corresponding to apex 646, indicating a high level of user engagement. After apex 654, a decline to baseline for user engagement is shown to occur. As a result of the first scene level of user engagement 654, the system or method discussed here is able to track in real-time or near real-time, a user's level of engagement in response to various content that may be presented.

Returning to expected pupil size and measured pupil size 622 for the second scene 612, second scene measured pupil size 636 is shown to be consistently lower than the second scene expected pupil size 634. This is reflected by second scene Δ pupil size 648 in Δ pupil size plot 642, which is shown to be below 0 mm for a majority of the second scene 612.

For example, according to some embodiments, second scene Δ pupil size 648 may reflect a difference between second scene measured pupil size 636 and second scene expected pupil size 634 that is roughly −2 mm on average. Moreover, there is a trough 650 in second scene Δ pupil size 648 corresponding to a calculated difference 640 between second scene measured pupil size 636 and second scene expected pupil size 634 at point 638 within the second scene 612 representing a point with the lowest level of user engagement.

As noted above, levels of user engagement are generally proportional to Δ pupil size. Accordingly, the second scene level of engagement 658 is shown to decrease from a baseline to a nadir 660 that corresponds to point 638 within the second scene 612. The second scene level of engagement 658 is then shown to increase a certain amount before the plot terminates. Thus, it may be possible to identify a segment corresponding to point 638 within a given scene that causes the most user disengagement (e.g., repulsions, disinterest, disaffection, and/or boredom, etc.). This feedback could be beneficial to content creators for identifying segments within VR scenes apparently disengage HMD users.

Figure 7A:
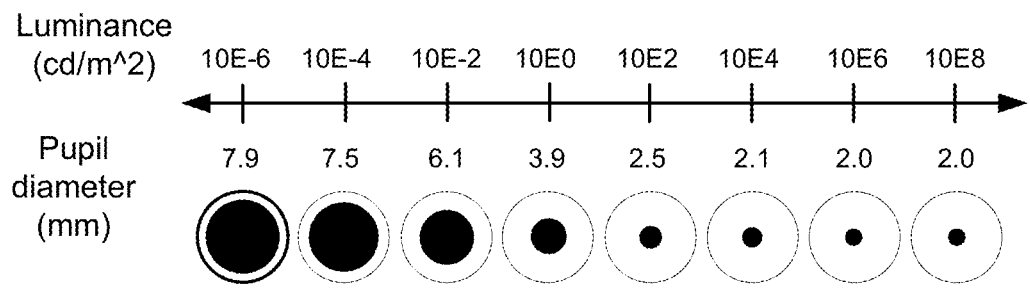
FIGS. 7A-C shows relationships between luminance and pupil sizes that may be used to establish expected pupil size.
Figure 7B:
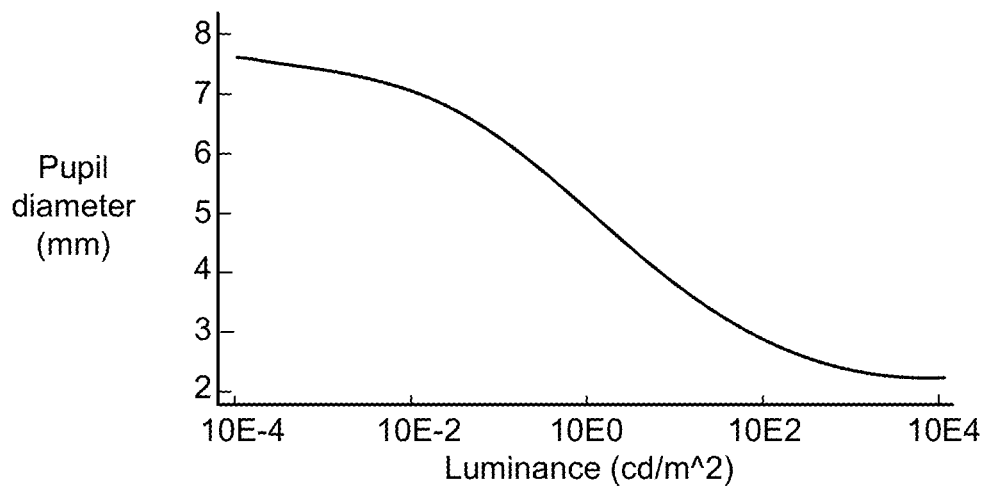
Figure 7C:
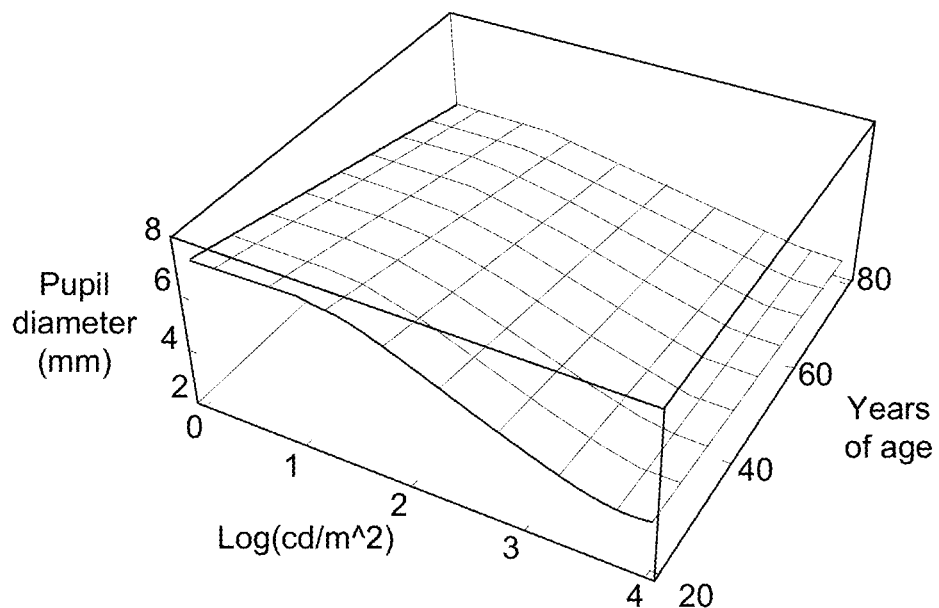

FIGS. 7A-C shows relationships between luminance and pupil sizes that may be used to establish expected pupil size. For example, FIG. 7A shows a general relationship between a range of luminance from 10E-6 cd/m$^2$ to 10E8 cd/m$^2$ with pupil size. FIG. 7B shows a similar relationship that is the result of an equation that may be used for establishing expected pupil size given a particular luminance and age of user. FIG. 7C illustrates pupil size as a function of luminance and age.

Each of the relationships shown in FIGS. 7A-C is well established in the art and will not be discussed in detail here. However, it is appreciated here that expected pupil size may be obtained without using a pupillary response test segment or test sequence. For example, expected pupil sizes for a range of luminance of VR content that is to be displayed may be obtained from the relationships given in FIGS. 7A-C, according to some embodiments. In other embodiments, expected pupil size may be calculated from both pupillary response test segments and the exemplary relationships shown in FIGS. 7A-C.

Figure 8:
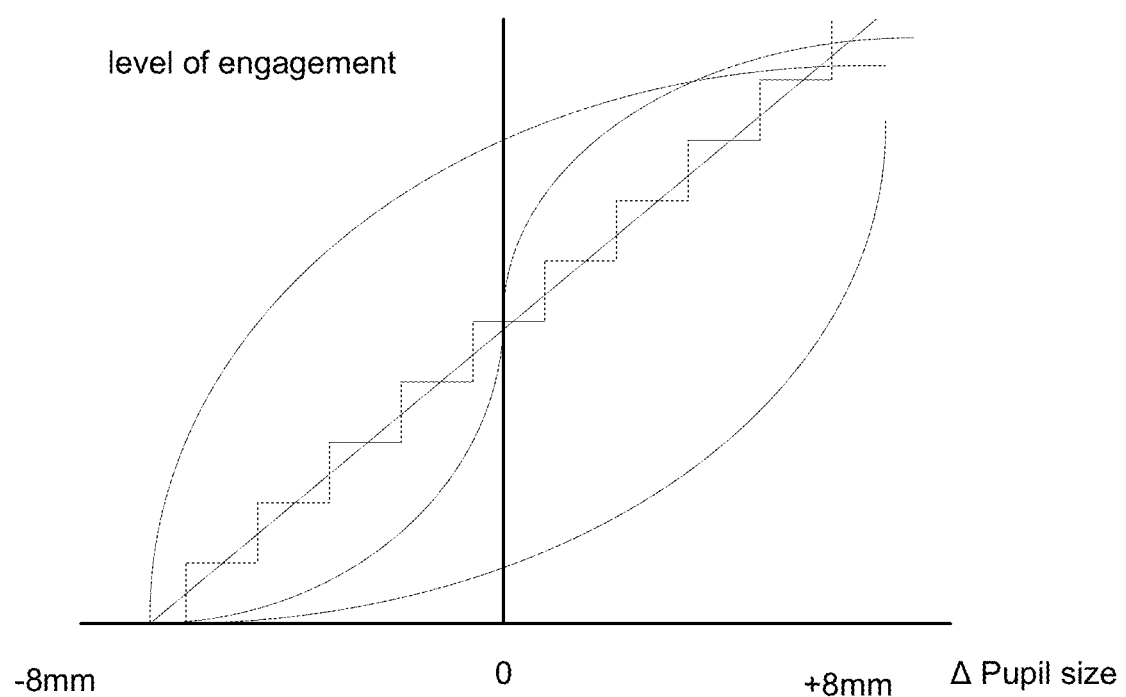
FIG. 8 illustrates exemplary relationships describing levels of user engagement as functions of Δ pupil size.

FIG. 8 illustrates exemplary relationships describing levels of user engagement as functions of Δ pupil size. Generally speaking, a user's level engagement is proportional a calculated Δ pupil size, where Δ pupil size is typically defined as a difference between a measured pupil size and an expected pupil size, according to certain embodiments. For example, if a user's pupil size is greater than what an expected pupil size is, Δ pupil size is to be positive, which correlates with a relatively higher level of user engagement. On the other hand, if a user's pupil size is less than what it is expected to be, the resulting Δ pupil size will be negative and correlate with a relatively lower level of user engagement. If there is a zero, near-zero, or negligible difference between the user's pupil size and an expected pupil size, Δ pupil size will likewise be zero, near-zero—or negligible.

In certain embodiments, a Δ pupil size of zero will correlate with a baseline level of user engagement. In these and other embodiments, the baseline level of user engagement serves to indicate a user state that is neither measurably interested, nor measurably disinterested. The baseline level of user engagement may also signify that the user is neither exerting significant mental or cognitive effort, nor being mentally or cognitively disengaged. Examples of a baseline level of user engagement may include an average user's state while being presented an opening credit scene, navigating a familiar virtual terrascape, performing routine tasks within a virtual reality environment, etc.

The x-axis in the graph of FIG. 8 is shown represent Δ pupil size that ranges from about −8 mm to about +8 mm. The y-axis of the same graph represents user engagement on an arbitrary scale. As shown in FIG. 8, there are a number of relationships that can be used to describe or relate Δ pupil size with a level of user engagement. For example, a linear relationship, an exponential relationship, a relationship defined by a step-function, a logarithmic relationship, and a sigmoidal relationship may all be used to describe or correlate levels of user engagement from Δ pupil size. Of course, the relationships shown in FIG. 8 are not meant to be exhaustive or limiting. As a result, a number of additional relationships may be used with the method and system described here to relate Δ pupil size to levels of engagement that do not depart from the scope or spirit of the embodiments.

Generally speaking, it should be noted that user engagement may be quantified for a given VR segment as an instantaneous level of user engagement, accumulative level of user engagement, and/or average level of user engagement, etc. Each of these may be a function of an instantaneous Δ pupil size (e.g., the difference between measured and expected pupil sizes at an instant in time), cumulative Δ pupil size (e.g., area under a curve for Δ pupil size in units of mm*seconds), or average Δ pupil size, respectively. As a result, FIG. 8 could be representative of not only instantaneous level of user engagement, but also cumulative engagement and average engagement. For example, FIG. 8 may also represent cumulative Δ pupil size versus cumulative engagement and average Δ pupil size versus average engagement, in addition to representing instantaneous Δ pupil size versus instantaneous engagement.

Figure 9:
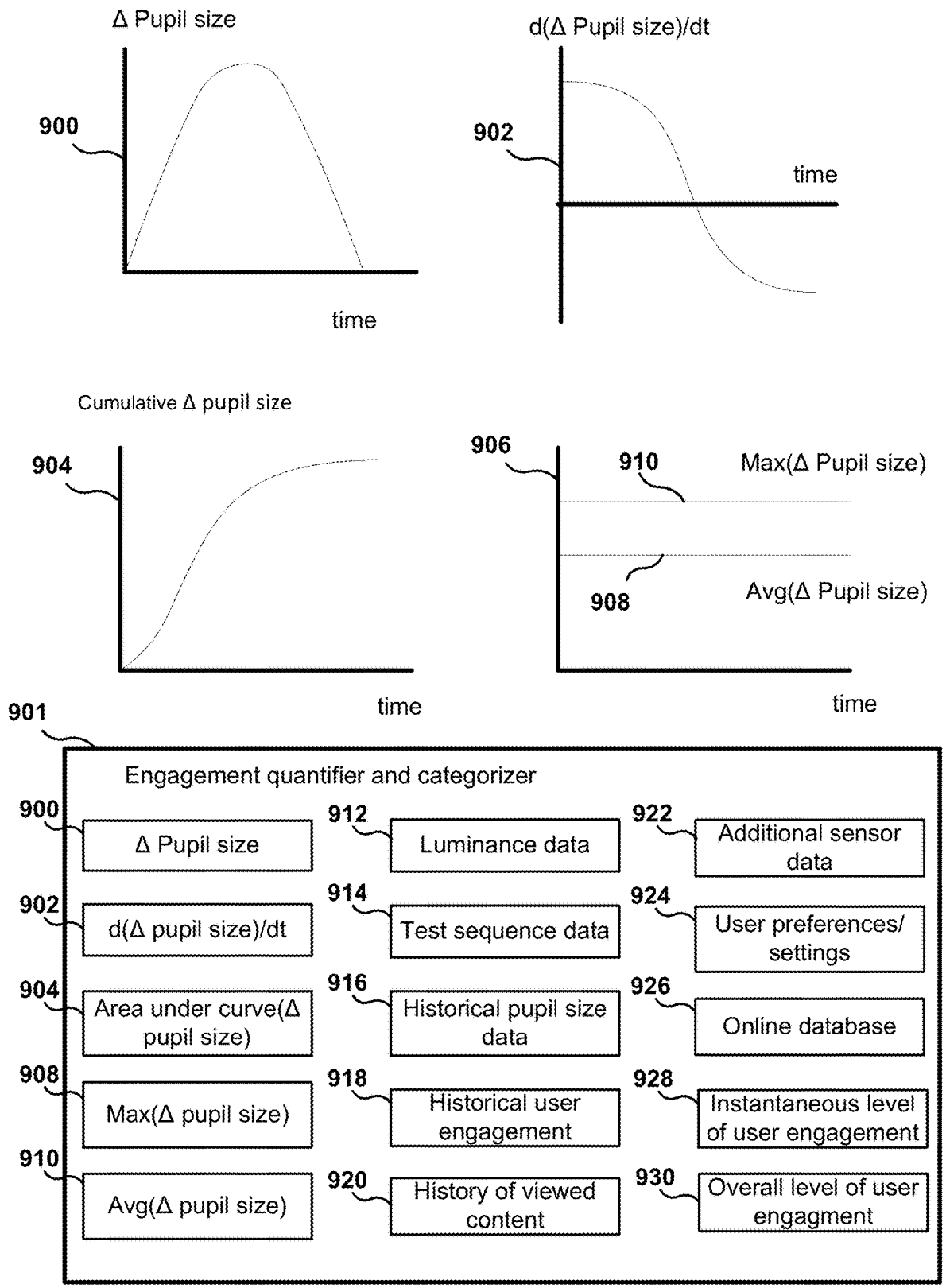
FIG. 9 illustrates additional components and metrics that may be used to quantify user engagement.

FIG. 9 illustrates additional components or metrics that may be used to quantify user engagement. For example, plot 900 shows an exemplary plot of a user's Δ pupil size over a period of time. Plot 902 shows a corresponding plot d(Δ pupil size)/dt over the same period. That is, plot 902 shows the slope of curve shown in plot 900, which may be useful for determining a rate of change of Δ pupil size. For example, a higher rate of change of Δ pupil size (e.g., d(Δ pupil size)/dt is large and positive, for example, d(Δ pupil size)/dt=+0.2 mm/s) may indicate that the user is attracted more instantaneously or that the user's interest is more immediately piqued, according to some embodiments. If a smaller rate of change in Δ pupil size (e.g., d(Δ pupil size)/dt is small and positive, for example, d(Δ pupil size)/dt=+0.02 mm/s) is detected, it may indicate that the user's interest, appeal, attraction, or cognitive engagement is increased more gradually. In some embodiments, this may suggest that the user 'warms up' or 'learns to appreciate' the corresponding content more so than he or she is immediately drawn to the content.

On the other hand, if the rate of change in Δ pupil size is large and negative (e.g., d(Δ pupil size)/dt=−0.2 mm/s), this may indicate that the user is repulsed, put-off, or otherwise experiences immediate displeasure in response to viewing the corresponding content. However, if the rate of change in Δ pupil size is less negative (e.g., d(Δ pupil size)/dt is small and negative, for example, d(Δ pupil size)/dt=−0.005) is detected, it may be indicative that user is growing tired, bored, or disinterested in a more gradual manner. As a result, d(Δ pupil size)/dt may be used in certain embodiments to inform a categorization of a user's state in response to content displayed by an HMD.

Also shown in FIG. 8 is a plot 904 that represents the 'area under the curve' of the plot 900 of Δ pupil size. Generally speaking, area under the curve can be interpreted as accumulated Δ pupil size, or total Δ pupil size over a period of time, and may be measured in terms of mm*seconds. Plot 904 may be useful in some embodiments for quantifying the total or overall difference in measured and expected pupil sizes for a given period associated with a VR scene. In the example, shown, accumulated Δ pupil size is shown to increase quickly towards the beginning of the segment and less quickly towards the end of the segment in time, in accordance with plot 900.

Thus, plot 904 may be used to determine a cumulative impression of a segment to a user. For example, if plot 900 showed a Δ pupil size that spent as much time in positive territory as it does in negative territory (e.g., the segment resulted in a comparable amount of interest and disinterest), then cumulative Δ pupil size may equal about 0 mm*seconds. Thus, even if the same segment is found to have resulted in high user engagement, it may be useful to know the user's overall impression of the segment by taking into account the cumulative Δ pupil size.

Generally speaking, if a given segment is determined to have a high cumulative Δ pupil size (e.g., 10 mm*seconds), it may indicate that the user had a high overall level of engagement to the segment. Conversely, if a given segment is determined to have a low cumulative pupil size (e.g., −20 mm*seconds), there may be an indication that the user had a low overall level of engagement to the segment, even if portions of it resulted in a high level of engagement for specific moments.

Closely related to cumulative Δ pupil size shown in plot 904 is the average Δ pupil size 908 shown in plot 906, which can be interpreted to be dividing cumulative Δ pupil size by time. Average Δ pupil size may be useful in a similar manner as cumulative Δ pupil size may be. Also shown in plot 906 is a max Δ pupil size, which represents a local or global maximum of Δ pupil size from plot 900. Max Δ pupil size may be useful in certain embodiments to determine a maximum level of engagement for the user with respect to the VR segment. For example, a first segment and a second segment are associated with average Δ pupil size that are nearly the same, but the first segment is determined to have a higher max Δ pupil size than the second, then such data may indicate that the first segment caused the user to have a higher instantaneous level of engagement than the second segment caused.

The metrics and data shown in each of plots 900-906 may be captured and used by engagement quantifier and categorizer 901. Engagement quantifier and categorizer is shown to result in instantaneous level of user engagement 928 and/or overall level of user engagement 930, both of which may be used by content creators to better cater to their audiences. In addition, engagement quantifier and categorizer 901 is also shown to use luminance data 912, test sequence data 914, historical pupil size data 916 historical user engagement 918, history of viewed content 920, additional sensor data 922, user preferences/settings 924, and data from online database 926.

As described above, luminance data 912 may include data on the luminance of a given VR scene, against which expected pupil size may be calculated. Also discussed above, test sequence data 914 includes pupillary response data from a test sequence. Historical pupil size data 916 may include a record of a user's pupillary response to previously viewed content and historical user engagement 918 may similarly include a record of a user's levels of engagement to previously viewed content. Further, engagement quantifier and categorizer 901 is shown to include a history of viewed content 920, which may include a record of the type and duration of content that was previously viewed for a user.

Engagement quantifier and categorizer 901 is also shown to use additional sensor data 922, data obtained from user preferences/settings 924, and data from an online database 926 for quantifying and categorizing levels of user engagement. Additional sensor data 922 may include measurements for additional physiological states of a user, including the user's heartbeat, brain waves, skin conductance (e.g., moisture levels), eye shape, gaze information, among others, and be incorporated into a quantification and categorization of a user's state or level of engagement. As a result, a number of sources of data such as those shown in FIG. 9 may be used to quantify and categorize a user's level of engagement for a VR segment or scene.

Figure 10:
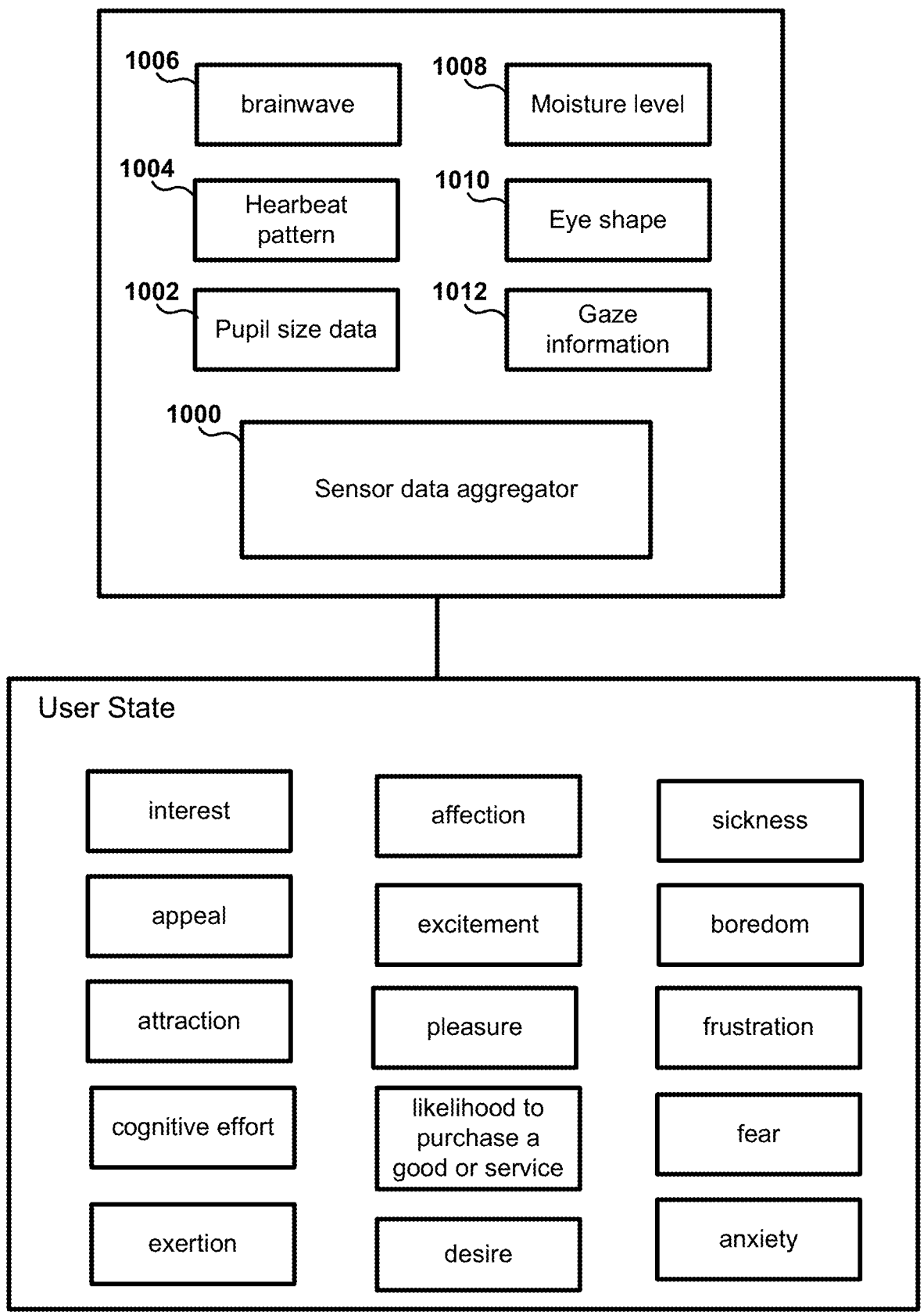
FIG. 10 illustrates a scheme of identifying various user states from various sensor data.

FIG. 10 illustrates a scheme of identifying various user states from various sources of sensor data. As mentioned above, data from other sensors besides pupil size data 1002 may be aggregated or fused by a sensor data aggregator 1000. As non-delimiting examples, the types of data that sensor data aggregator 1000 is able to incorporate includes heartbeat pattern 1004 data, brainwave data 1006, moisture level data 1008 of a user's skin, eye shape data 1012, and gaze information 1012.

According to some embodiments, sensor data aggregator 1000 may combine, fuse, or incorporate data from these sources of data 1004-1012 along with pupil size data 1002 to provide information regarding user's state with respect to interest, appeal, attraction, cognitive effort, exertion, affection, excitement, pleasure, likelihood to purchase a good or service, desire, sickness, dizziness, vertigo, boredom, frustration, fear, anxiety, among others. As a result, the embodiments presented here may use sensor data from a variety of sources in addition to pupil size measurements to estimate, quantify, and/or categorize a number of user states.

Figure 11:
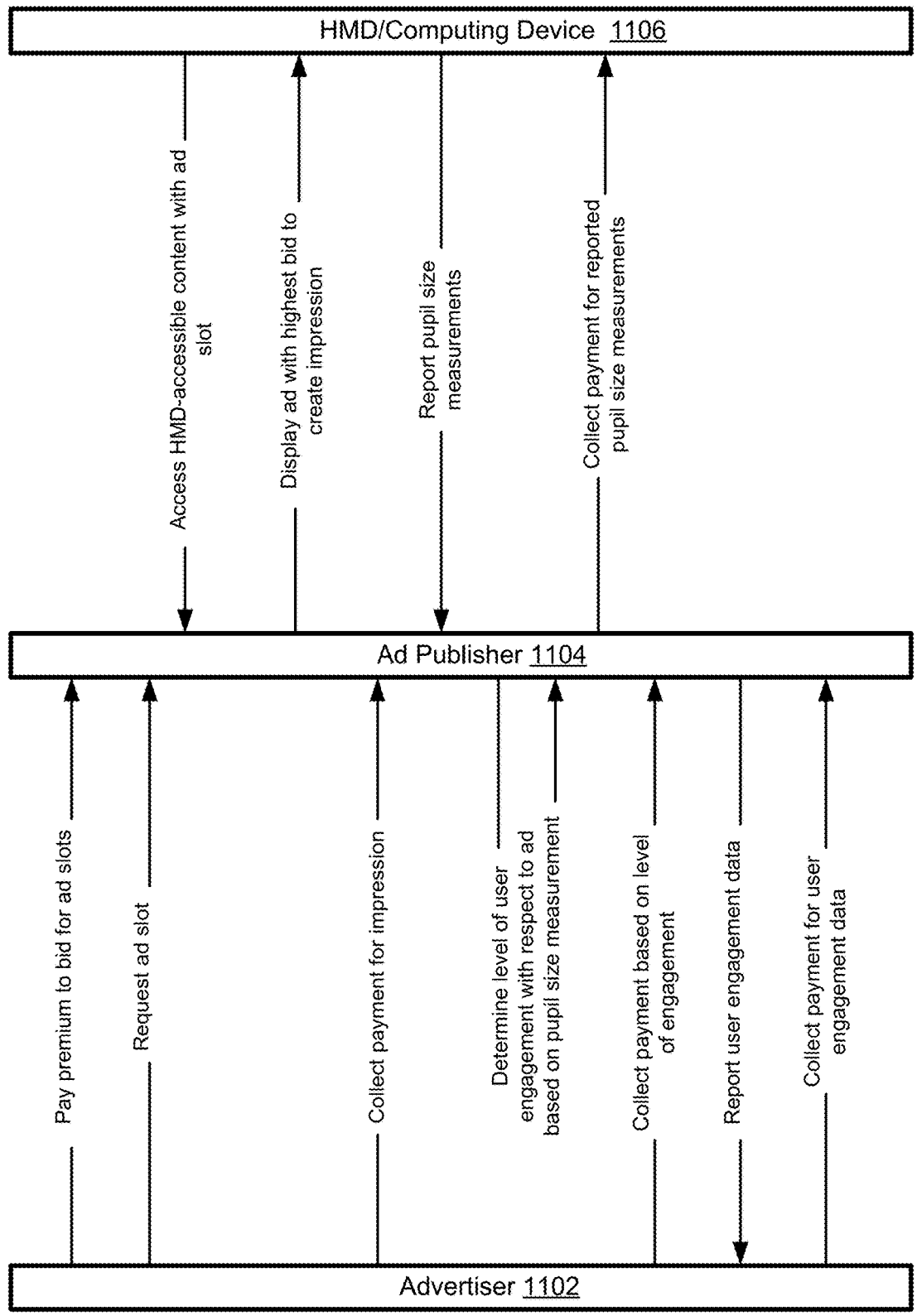
FIG. 11 illustrates an embodiment of a method of advertising within a VR environment using a pay-per-engagement model.

FIG. 11 illustrates an embodiment of a method of advertising within a VR environment using a 'pay-per-engagement' or 'pay-per-appeal' model. According to the model shown, an advertiser 1102 pays a premium to bid for ad slots that are to be displayed to an HMD user via an HMD/computing device 1106, for example, while viewing a VR scene. The advertiser proceeds to request the ad slot by submitting a bid for the ad slot. According to the embodiment shown, the HMD/computing device 1106 is configured to access HMD-accessible content including the ad slot. The ad slot will be displayed to the HMD/computing device 1106 with an ad with the highest bid for creating an impression. As a result, the ad publisher 1104 will collect a payment for the impression from the advertiser 1102.

According to the embodiment of FIG. 11, the HMD/computing device 1106 then reports pupil size measurements of the user in response to viewing the ad displayed in the ad slot to the ad publisher 1104. Ad publisher 1104 is enabled to determine a level of engagement of the user to the ad based on the reported pupil size measurements and collect a payment in accordance with the level of engagement of the user to the ad.

Optionally or additionally, certain embodiments may include a step having HMD/computing device 1106 collect a payment for reporting pupil size measurements and data to the ad publisher 1104. As a result, an HMD user may be compensated or credited for allowing the HMD to record and report his or her pupil size measurements and data to the ad publisher 1104. Furthermore, certain embodiments may include a step having the ad publisher 1104 report user engagement data to the advertiser 1102. The user engagement data, which includes data related to whether users are engaged with the ad or not, may be valuable to the advertiser 1102. As a result, ad publisher 1104 may collect a payment for the user engagement data.

Figure 12A:
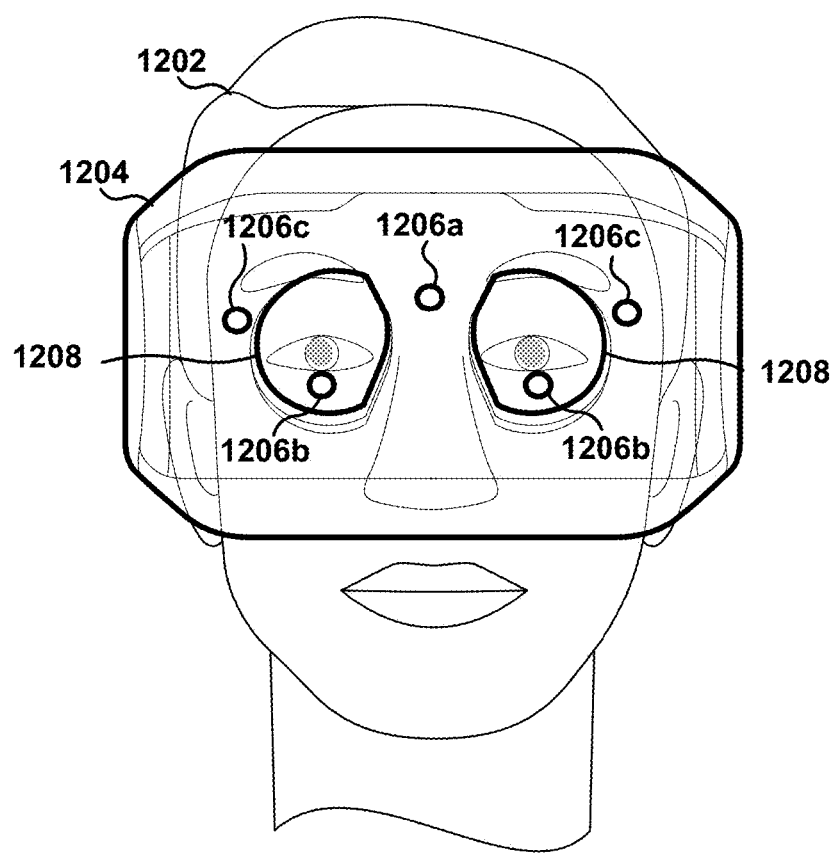
FIGS. 12A-B illustrates an embodiment of a head mounted display (HMD) that is capable of measuring pupil size using image capture devices.
Figure 12B:
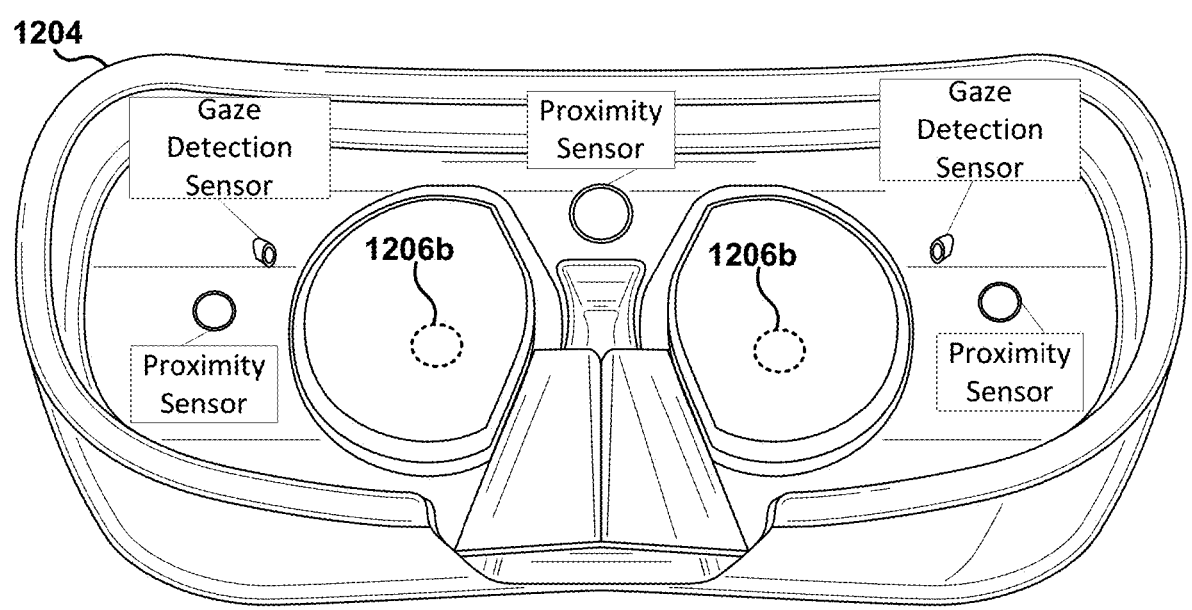

FIGS. 12A-B illustrates an embodiment of a head mounted display (HMD) 1204 that is capable of measuring pupil size of a user 1202 using image capture devices 1206a-c. For example, FIG. 12A shows a user 1202 wearing the HMD 1204 having a plurality of image capture devices 1206a-c. In certain embodiments, the image capture device 1206a is located between the two eyes of the user 1202 and has a field of view that spans one or both eyes of the user 1202. The embodiment may also include image capture devices 1206b that are located behind a display associated with the HMD.

For embodiments having image capture device 1206b that are located behind a display, the display that is used may be optically translucent for light that is reflected from the eyes of user 1202. For example, the displays associated with the HMD 1204 may be optically translucent for infrared (IR) light, or polarized light. As a result, light that is incident on the eyes of user 1202 may pass through the displays associated with the HMD 1204 and be captured by image capture devices 1206b. In other embodiments, the image capture devices 1206c may be located outside of the view area 1208 of the HMD 1204 and be configured to capture images of the eyes of the user 1202 from oblique angles. It is also contemplated that certain embodiments will include all of image capture devices 1206a-c, or a portion of them.

Generally speaking, image capture devices 1206a-c should have a high enough image capture frame rate to detect pupil size changes that may occur quickly. In certain contemplated embodiments, the image capture devices 1206a-c may be capable of video capture of about 30 to 240 frames per second (fps) or more. Moreover, image capture devices 1206a-c that are contemplated may have imaging resolution that is high enough to detect changes in pupil size (e.g., between about 1-40 megapixels).

FIG. 12B shows an additional view of HMD 1204. For example, HMD 1204 is shown to include proximity sensors and gaze detection sensors in addition to image capture devices 1206b. Image capture devices 1206b are shown to be disposed behind displays that are associated with the HMD 1204. As noted above, proximity sensors and gaze detection sensors may be used to estimate the effective luminance that the eyes of HMD user 1202 experiences. For example, depending on how proximate HMD user 1202 is to the viewing areas 1208, the effective luminance experience by the eyes of HMD user 1202 may be affected. As a result, proximity data obtained by proximity sensors may be used by, for example, luminance module 114 of FIGS. 1A and 1B calculate an effective luminance of a given VR scene.

Likewise, gaze detection sensors may provide data to luminance module 114 to determine the luminance each eye is experiences at any given moment, according to some embodiments. As discussed earlier, effective luminance may depend upon where HMD user 1202 is looking within a VR scene. As a result, gaze detection sensors may provide data to better estimate the amount or intensity of light that a user experiences for a given VR scene depending upon where the HMD user 1202 is gazing at.

Figure 13:
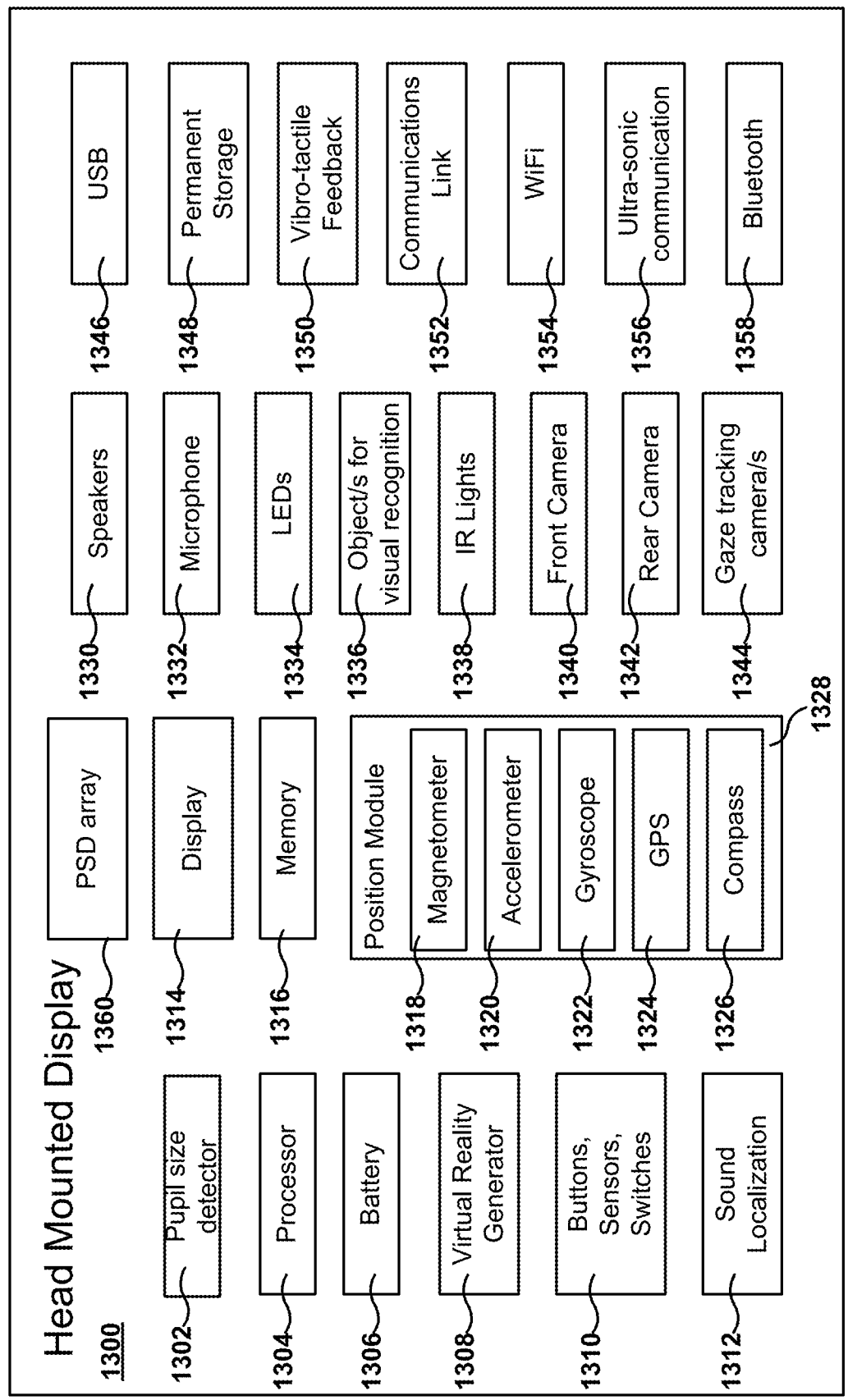
FIG. 13 illustrates an additional embodiment of a head mounted display (HMD) that may be used to quantify and categorize user engagement by measuring pupil size.

FIG. 13 illustrates and additional embodiment of an HMD 1300 that may be used with the presented method and/or system. HMD 1300 includes hardware such as pupil size detector 1302, a processor 1304, battery 1306, virtual reality generator 1308, buttons, sensors, switches 1310, sound localization 1312, display 1314, and memory 1316. HMD 1302 is also shown to include a position module 1328 that comprises a magnetometer 1318, an accelerometer 1320, a gyroscope 1322, a GPS 1324, and a compass 1326. Further included on HMD 102 are speakers 1330, microphone 1332, LEDs 1334, object/s for visual recognition 1336, IR lights 1338, front camera 1340, rear camera 1342, gaze tracking camera/s 1344, USB 1346, permanent storage 1348, vibro-tactile feedback 1350, communications link 1352, WiFi 1354, ultra-sonic communication 1356, Bluetooth 1358, and photo-sensitive diodes (PSD) array 1360.

Although the method operations were described in a specific order, it should be understood that other housekeeping operations may be performed in between operations, or operations may be adjusted so that they occur at slightly different times, or may be distributed in a system which allows the occurrence of the processing operations at various intervals associated with the processing.

One or more embodiments can also be fabricated as computer readable code on a computer readable medium. The computer readable medium is any data storage device that can store data, which can be thereafter be read by a computer system. Examples of the computer readable medium include hard drives, network attached storage (NAS), read-only memory, random-access memory, CD-ROMs, CD-Rs, CD-RWs, magnetic tapes and other optical and non-optical data storage devices. The computer readable medium can include computer readable tangible medium distributed over a network-coupled computer system so that the computer readable code is stored and executed in a distributed fashion.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the embodiments are not to be limited to the details given herein, but may be modified within the scope and equivalents of the appended claims.

What is claimed is:

1. A computer-implemented method for determining user engagement of a head mounted display (HMD) user in response to being presented a virtual reality (VR) scene, comprising:
   presenting the VR scene to the HMD user via a display of an HMD;
   capturing one or more images of an eye of the HMD user while the HMD user is wearing the HMD and being presented the VR scene, the one or more images usable to detect a pupil size of the eye of the HMD user in response to viewing the VR scene;
   analyzing the one or more images for obtaining a pupil size measurement of the eye of the HMD user;
   normalizing the pupil size measurement against a content of the VR scene to obtain a normalized pupil size measurement, wherein said normalizing the pupil size measurement is based on a calibration of the HMD user that includes displaying a test segment to the HMD user via the display of the HMD, the test segment including a series of reference images having a varying luminance and capturing a plurality of images of the eye of the HMD user in response to the HMD user viewing the test segment for determining an expected pupil size of the HMD user, the normalized pupil size measurement describes a deviation between the pupil size measurement and the expected pupil size;
   obtaining pupil size indicators usable to correlate normalized pupil size measurements with user engagement; and
   determining a level of user engagement based on the normalized pupil size measurement and the pupil size indicators.

2. The computer-implemented method of claim 1, wherein said analyzing the one or more images further includes obtaining pupil size change measurements, wherein the pupil size indicators are further usable to correlate pupil size change measurements with user engagement, and wherein determining the level of user engagement is further based on the pupil size change measurements.

3. The computer-implemented method of claim 1, wherein the level of user engagement is associable to particular one or more segments within the VR scene.

4. The computer-implemented method of claim 1, wherein the content type of the VR scene is based on one or more of a luminance, a brightness, a saturation, a gamma level, or a level of contrast of the VR scene.

5. The computer-implemented method of claim 1, further comprising:
   modifying, based on the level of user engagement, one or more parameters associated with the VR scene.

6. The computer-implemented method of claim 5, wherein said modifying the one or parameters associated with the VR scene is configurable to change a lighting of the VR scene, a resolution of the VR scene, a texture of the VR scene, a quantity of content items within the VR scene, a dynamism of the VR scene, a motion of objects within the VR scene, a difficulty of a task associated with the VR scene, a number of enemies within the VR scene, an ease of navigation of the VR scene, a pace of the VR scene, or a difficulty of progressing within the VR scene.

7. The computer-implemented method of claim 1, wherein the level of user engagement of the HMD user with respect to the VR scene includes one or more metrics associated with a level of interest, a level of appeal, a level of attraction, a level of cognitive effort, a level of exertion, a level of affection, a level of excitement, a level of pleasure, a level of desire, a likelihood to purchase a good or service, a level of sickness, a level of dizziness, a level of vertigo, a level of boredom, a level of frustration, a level of fear, and a level of anxiety of the HMD user with respect to the VR scene.

8. The computer-implemented method of claim 1, further comprising:

obtaining sensor data from one or more sensors associated the HMD, wherein said determining the level of user engagement is further based on the sensor data.

9. The computer-implemented method of claim 1, wherein the one or more sensors associated with the HMD include one or more of a gaze detector, a skin conductance sensor, an eye shape detector, a brainwave sensor, or a heartbeat pattern sensor.

10. A computer-implemented method for determining user engagement of a head mounted display (HMD) user in response to being presented a virtual reality (VR) scene, comprising:
   presenting the VR scene to the HMD user via a display of an HMD;
   capturing one or more images of an eye of the HMD user while the HMD user is wearing the HMD and being presented the VR scene, the one or more images usable to detect a pupil size of the eye of the HMD user in response to viewing the VR scene;
   analyzing the one or more images for obtaining a pupil size measurement of the eye of the HMD user;
   normalizing the pupil size measurement against a content of the VR scene to obtain a normalized pupil size measurement;
   wherein said normalizing the pupil size measurement involves comparing the pupil size measurement against an expected pupil size for obtaining the normalized pupil size measurement, the normalized pupil size measurement describing a deviation between the pupil size measurement and the expected pupil size, wherein said determining the level of user engagement is further based on the deviation between the pupil size measurement and the expected pupil size.

11. The computer-implemented method of claim 10, wherein a positive deviation is associable with relatively higher level of user engagement compared to that of a less positive deviation.

12. The computer-implemented method of claim 10, wherein the expected pupil size is based on one or more of a luminance of the VR scene, a content of the VR scene, a history of pupil size measurements for the HMD user, a viewing history of the HMD user, an age of the HMD user, a database of pupil size measurements from additional HMD users, or one or more algorithms for relating luminance with pupil size.

13. A computer-implemented method for determining user engagement of a head mounted display (HMD) user in response to being presented a virtual reality (VR) scene, comprising:
   presenting the VR scene to the HMD user via a display of an HMD;
   capturing one or more images of an eye of the HMD user while the HMD user is wearing the HMD and being presented the VR scene, the one or more images usable to detect a pupil size of the eye of the HMD user in response to viewing the VR scene;
   analyzing the one or more images for obtaining a pupil size measurement of the eye of the HMD user;
   normalizing the pupil size measurement against a content of the VR scene to obtain a normalized pupil size measurement;
   obtaining pupil size indicators usable to correlate normalized pupil size measurements with user engagement;
   determining a level of user engagement based on the normalized pupil size measurement and the pupil size indicators;
   wherein said normalizing the pupil size measurement includes,
      displaying a test segment to the HMD user via the display of the HMD, the test segment including a series of reference images having a varying luminance;
      capturing a plurality of images of the eye of the HMD user in response to the HMD user viewing the test segment for determining an expected pupil size of the HMD user;
      using the expected pupil size for said normalizing the pupil size measurement for obtaining the normalized pupil size measurement that describes a deviation between the pupil size measurement and the expected pupil size,
   wherein said determining the level of user engagement is further based on the deviation between the pupil size measurement and the expected pupil size.

14. The computer-implemented method of claim 13, wherein a positive deviation is indicative of a relatively higher level of user engagement than a less positive deviation.

15. A head mounted display (HMD) system for delivering a VR scene to an HMD user, comprising
   a display to present the VR scene to the HMD user;
   an image capture device to capture a first plurality of images of an eye of the HMD user, the first plurality of images usable to obtain pupil size measurements of the HMD user while the HMD user is being presented the VR scene;
   a network interface device to receive pupil size indicators, the pupil size indicators configured to correlate pupil size measurements of the HMD user to levels of engagement of the HMD user;
   a memory to store the first plurality of images of the eye of the HMD user and the pupil size indicators; and
   a computing device to analyze the first plurality of images of the eye of the HMD user to obtain pupil size measurements of the HMD user, to normalize the pupil size measurements against a content of the VR scene to obtain normalized pupil size measurements, and to determine a level of user engagement based on the normalized pupil size measurements and the pupil size indicators;
   wherein the display is configured to present a test segment including a series of images having varying luminance, wherein the image capture device is configured to capture a second plurality of images of the eye of the HMD user while the HMD user is being presented the test segment, wherein the second plurality of images are usable for said normalizing the pupil size measurements against the content of the VR scene.

16. The system of claim 15, wherein the computing device is configured to associate the level of user engagement with one or more segments within the VR scene.

* * * * *